US009522938B2

(12) United States Patent
Wald et al.

(10) Patent No.: US 9,522,938 B2

(45) Date of Patent: Dec. 20, 2016

(54) PHL P 5A DERIVATIVES HAVING REDUCED ALLERGENEITY AND RETAINED T-CELL REACTIVITY

(71) Applicant: Merck Patent GmbH, Darmstadt (DE)

(72) Inventors: Martin Wald, Hamburg (DE); Oliver Cromwell, Suesel-Fassendorf (DE); Andreas Nandy, Hamburg (DE); Helga Kahlert, Hamburg (DE); Bernhard Weber, Hamburg (DE); Helmut Fiebig, Schwarzenbek (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/146,364

(22) Filed: Jan. 2, 2014

(65) Prior Publication Data

US 2014/0255434 A1 Sep. 11, 2014

Related U.S. Application Data

(62) Division of application No. 10/559,272, filed as application No. PCT/EP2004/004848 on May 6, 2004, now Pat. No. 8,628,946.

(30) Foreign Application Priority Data

Jun. 4, 2003 (DE) ................................ 103 25 508

(51) Int. Cl.

*A61K 48/00* (2006.01)
*C07H 21/02* (2006.01)
*C07H 21/04* (2006.01)
*C12N 15/00* (2006.01)
*C12N 15/09* (2006.01)
*C12P 21/04* (2006.01)
*C07K 14/415* (2006.01)
*A61K 39/35* (2006.01)
*A61K 39/00* (2006.01)

(52) U.S. Cl.

CPC ............ *C07K 14/415* (2013.01); *A61K 39/35* (2013.01); *A61K 2039/55505* (2013.01); *A61K 2039/55561* (2013.01)

(58) Field of Classification Search

None

See application file for complete search history.

(56) References Cited

U.S. PATENT DOCUMENTS 5,840,316 A 11/1998 Singh et al.
8,628,946 B2 * 1/2014 Wald .................... C07K 14/415 435/243
2002/0064530 A1 5/2002 Sturaro et al.

FOREIGN PATENT DOCUMENTS

DE 19713001 A 10/1998
DE 19918682 A 10/2000
WO 03025009 A 3/2003

OTHER PUBLICATIONS

Metzler et al. 'Solution structure of~uman CTLA-4 and delineation of a CD80/CD86 binding site conserved in CD28.' Nature Structural Biol. 4:527-531, 1997.*

Bork et al. 'Powers and Pitfalls in Sequence Analysis: The 70% Hurdle.' Gen. Res. 10:398-400, 2000.*

Doerks et al. 'Protein annotation: detective work for function prediction.' Trends in Genetics. 14:248-250, 1998.*

Smith et al. The challenges of genome sequence annotation or "the devil is in the details". Nat. Biotech.15:1222-1223, 1997.*

Zolkipli et al. 'Randomized controlled trial of primary prevention of atopy using house dust mite allergen oral immunotherapy in early childhood.' J. Allerg. Clin. Immunol. 136(6):1541-1547, 20015.*

Schramm G. et al., Allergen Engineering: Variants of the Timothy Grass Pollen Allergen Phl p 5b With Reduced IgE-Binding Capacity But Conserved T Cell Reactivity: Feb. 15, 1999; Journal of Immunology, Williams & Wilkins Co., US, pp. 2406-2414, XP002216586, ISSN: 0022-1767.

Ong et al., "Mapping of the antigenic and allergenic epitopes of Lol p VB using gene fragmentation" Molec. Immunol. 32(4):295-302, 1995.

Muller et al., "Mapping of T-cell epitopes of Phl p 5: evidence for crossreacting and non-crossreacting T-cell epitopes within Phl p 5 isoallergens" Clin. Exp. Allerg. 28:1538-1548, 1998.

Bufe et al., "Major allergen Phl p Va (timothy grass) bears at least two different IgE-reactive epitopes" J. Allergy Clin Immunol. 94:173-181, 1994.

Ngo et al., "Computational Complexity, Protein Structure Prediction, and the Levinthal Paradox" The Protein Folding Problem and Tertiary Structure Prediction. Ed K. Merz and S. Le Grand, Boston: Birkhauser, 1994.491-495.

Blumenthal et al., in Allergens and Allergen Immunotherapy, 3rd Edition, 2004, pp. 37-51.

Winther et al., Allergen-specific immunotherapy in birch- and grass-pollen-allergic rhinitis. II. Side-effects, Allergy 55 (9):827-835, 2000.

* cited by examiner

*Primary Examiner* — Nora Rooney

(74) *Attorney, Agent, or Firm* — Miller, White, Zelano, Branigan, P.C.

(57) ABSTRACT

The present invention relates to the preparation and use of variants of the group 5 allergen of the Pooideae which are characterised by reduced IgE reactivity compared with the known wild-type allergens and at the same time by substantially retained reactivity with T lymphocytes. These hypoallergenic allergen variants can be employed for the specific immunotherapy (hyposensitisation) of patients having grass pollen allergy or for the preventative immunotherapy of grass pollen allergies.

20 Claims, 11 Drawing Sheets

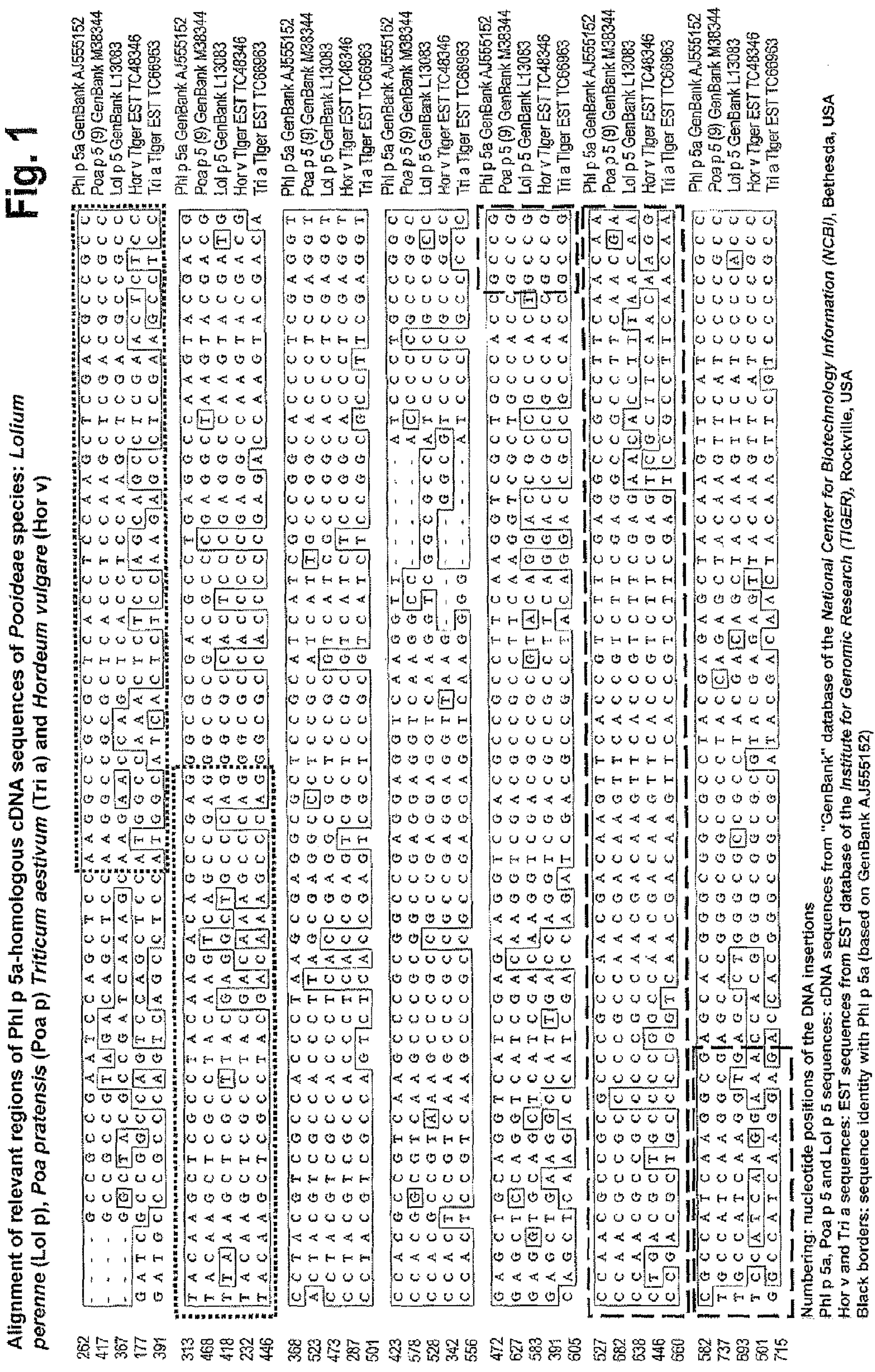
Fig. 1
Alignment of relevant regions of Phl p 5a-homologous cDNA sequences of Pooideae species: Lolium perenne (Lol p), Poa pratensis (Poa p) Triticum aestivum (Tri a) and Hordeum vulgare (Hor v)
Phl p 5a GenBank AJ555152
Poa p 5 (9) GenBank M38344
Lol p 5 GenBank L13083
Hor v Tiger EST TC48346
Tri a Tiger EST TC66963
Numbering: nucleotide positions of the DNA insertions
Phl p 5a, Poa p 5 and Lol p 5 sequences: cDNA sequences from "GenBank" database of the National Center for Biotechnology Information (NCBI), Bethesda, USA
Hor v and Tri a sequences: EST sequences from EST database of the Institute for Genomic Research (TIGER), Rockville, USA
Black borders: sequence identity with Phl p 5a (based on GenBank AJ555152)
Dotted borders: deletion corresponding to amino acids 94-113 (based on GenBank AJ555152)
Dashed borders: deletion corresponding to amino acids 175-198 (based on GenBank AJ555152)

**Alignment of Phl p 5a-homologous amino acid sequences (relevant sequence regions, deduced from DNA sequences) of Pooideae species: *Lolium perenne* (Lol p), *Poa pratensis* (Poa p) *Triticum aestivum* (Tri a) and *Hordeum vulgare* (Hor v)**

```
169 P P A D K Y R T F V A T F G A A S N K A F A E G L S G E P K  Phl p 5a GenBank AJ555152
324 P A A N K Y K T F V A T F G A A S N K A F A E A L S T E P K  Poa p 5 (9) GenBank M38344
286 P P A D K Y K T F V E T F G T A T N K A F V E G L A S - - -  Lol p 5 GenBank L13083
82  P P A D K Y K T F E A T F A A A S N K A F A E V L K G A A T  Hor v TIger EST TC48346
296 P P A D K Y K T F E A T F S A A S N X A F A D V L K A A A S  Tri a TIger EST TC66963

259 G - - A A E S S S K A A L T S K L D A A Y K L A Y K T A E G  Phl p 5a GenBank AJ555152
414 G - - A A V D S S K A A L T S K L D A A Y K L A Y K S A E G  Poa p 5 (9) GenBank M38344
367 - - - G Y A D Q S K N Q L T S K L D A A L K L A Y E A A Q G  Lol p 5 GenBank L13083
172 G Q I A G Q S S S M A K L S S S L E L S Y K L A Y D K A Q G  Hor v TIger EST TC48346
386 G Q M P A Q S A S M A S L S K S L E A S Y K L A Y D K A Q G  Tri a TIger EST TC66963

343 A T P E A K Y D A Y V A T L S E A L R I I A G T L E V H A V  Phl p 5a GenBank AJ555152
498 A T P E A K Y D D Y V A T L S E A L R I I A G T L E V H G V  Poa p 5 (9) GenBank M38344
448 A T P E A K Y D A Y V A T L T E A L R V I A G T L E V H A V  Lol p 5 GenBank L13083
262 A T P E A K Y D A Y V A T L T E S L R V I S G T L E V H S V  Hor v TIger EST TC48346
476 A T P E T K Y D T Y V A S L T E S L R V I S G A F E V H S V  Tri a TIger EST TC66963

433 K P A A E E V K V - - I P A G E L Q V I E K V D A A F K V A  Phl p 5a GenBank AJ555152
588 K P A A E E V K A - - T P A G E L Q V I D K V D A A F K V A  Poa p 5 (9) GenBank M38344
538 K P A A E E V K V G A I P A A E V Q L I D K V D A A Y R T A  Lol p 5 GenBank L13083
352 K P A A E E V K - - G V P A G E L K A I D Q V D A A F R T A  Hor v TIger EST TC48346
566 K P A A E E V K G X X I P A P Q L K T I D Q I D A A Y R T A  Tri a TIger EST TC66963
```

FIG. 2B

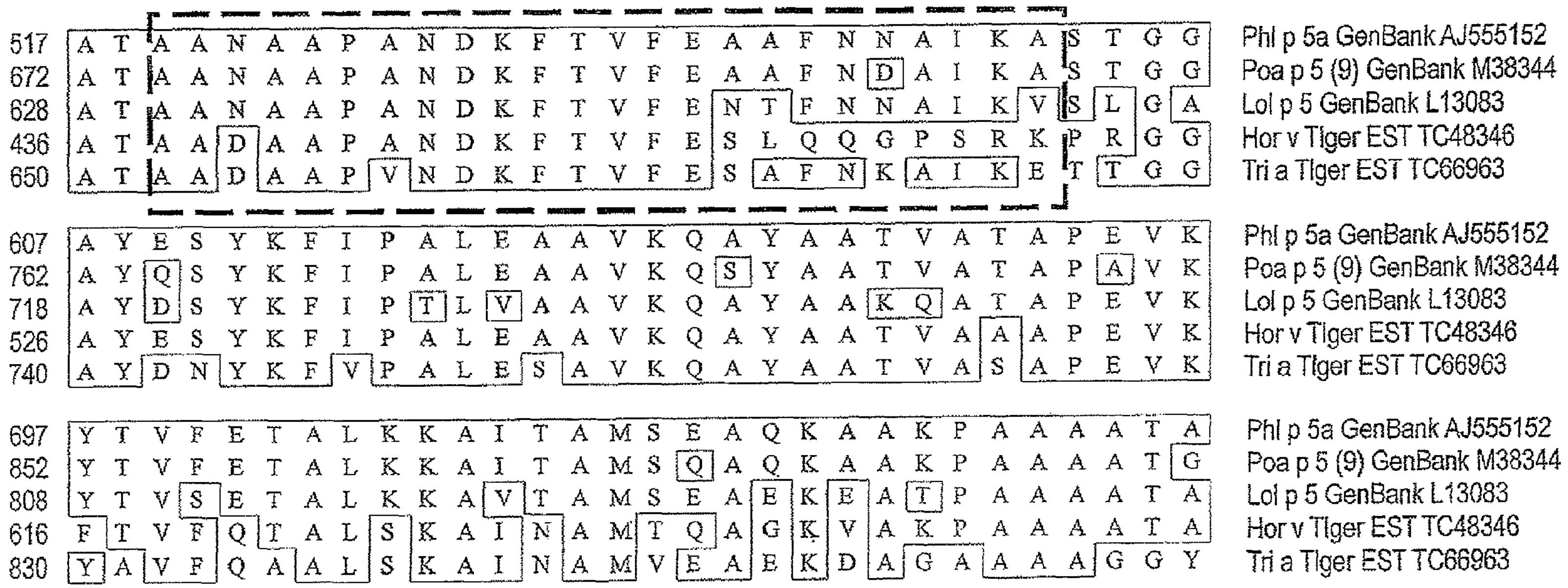

Numbering: nucleotide positions of the DNA insertions

Phl p 5a, Poa p 5 and Lol p 5 sequences: cDNA sequences from “GenBank“ database of the *National Center for Biotechnology Information (NCBI)*, Bethesda, USA Hor v and Tri a sequences: EST sequences from EST database of the *Institute for Genomic Research (TIGER)*, Rockville, USA Black borders: sequence identity with Phl p 5a (based on GenBank AJ555152)
Dotted borders: deletion corresponding to amino acids 94-113 (based on GenBank AJ555152)
Dashed borders: deletion corresponding to amino acids 175-198 (based on GenBank AJ555152)

SDS-PAGE of purified deletion mutants in the form of histidine fusion proteins

1) Marker
2) rPhl p 5a wt (His)
3) Phl p 5a DM-Δ94-113 (His)
4) Phl p 5a DM-Δ94-113, 175-198 (His)
5) Phl p 5a DM-Δ175-198 (His)
6) Marker

SDS-PAGE of the purified non-fusion proteins Phl p 5a DM-Δ94-113, 175-198 and rPhl p 5a wt (top) and identity test with αPhl p 5 antibodies (bottom)

αPhl p 5 mAb Apha-1D11 binds region 175-198 (only rPhl p 5a wt is positive)

αPhl p 5a mAb Apha-3B2 binds a joint epitope of the two Phl p 5a molecules (both proteins positive)

(mAb: monoclonal antibody)

Analytical SEC of deletion mutant Phl p 5a DM-Δ94-113, 175-198 and of recombinant wild type Phl p 5a (purified non-fusion proteins)

Column: Superdex 75 HR10/ 30 (Amersham Biosciences, Uppsala, Sweden)
Eluent: PBS
Arrow: exclusion volume

Non-denaturing isoelectric focusing of deletion mutant Phl p 5a DM-Δ94-113, 175-198 and of recombinant wild type Phl p 5a (purified non-fusion proteins)

1) IEF-Marker
2) rPhl p 5a wt
3) Phl p 5a DM-Δ94-113, 175-198 pI rPhl p 5a wt = 8.7
pI rPhl p 5a DM-Δ94-113, 175-198 = 6.4

Strip test for checking the IgE binding ability of Phl p 5a deletion mutants (non-denaturing)

P: sera of clinically defined grass pollen allergy sufferers

Determination of the reduced IgE reactivity of Phl p 5a deletion mutants by means of the EAST inhibition test with two representative single sera (a and b) and a serum pool (c)

Determination of the hypoallergeneity of Phl p 5a deletion mutant Phl p 5a DM-Δ94-113, 175-198 by means of the basophil activation test with basophils of six different grass pollen allergy sufferers (P)

SEQUENCE LISTING

<160> NUMBER OF SEQ ID NOS: 22

<210> SEQ ID NO 1
<211> LENGTH: 855
<212> TYPE: DNA
<213> ORGANISM: Phleum pratense

<400> SEQUENCE: 1

```
gccgatctag gctacggccc ggccacccca gctgccccgg ccgccggcta cacccccgcc      60

gccccggccg gagcggagcc agcaggtaag gcgacgaccg aggagcagaa gctgatcgag     120

aagatcaacg ccggcttcaa ggcggccttg gccgctgccg ccggcgtccc gccagcggac     180

aagtacagga cgttcgtcgc aaccttcggc gcggcctcca acaaggcctt cgcggagggc     240

ctctcgggcg agcccaaggg cgccgccgaa tccagctcca aggccgcgct cacctccaag     300

ctcgacgccg cctacaagct cgcctacaag acagccgagg gcgcgacgcc tgaggccaag     360

tacgacgcct acgtcgccac cctaagcgag gcgctccgca tcatcgccgg caccctcgag     420

gtccacgccg tcaagcccgc ggccgaggag gtcaaggtta tccctgccgg cgagctgcag     480

gtcatcgaga aggtcgacgc cgccttcaag gtcgctgcca ccgccgccaa cgccgcgccc     540

gccaacgaca agttcaccgt cttcgaggcc gccttcaaca acgccatcaa ggcgagcacg     600

ggcggcgcct acgagagcta caagttcatc cccgccctgg aggccgccgt caagcaggcc     660

tacgccgcca ccgtcgccac cgcgccggag gtcaagtaca ccgtctttga gaccgcgctg     720

aaaaaggcca tcaccgccat gtccgaggcc cagaaggctg ccaagcccgc tgccgctgcc     780

accgccaccg caacctccgc cgttggcgcg gccaccggcg ccgccaccgc cgctactggt     840

ggctacaaag tctga                                                      855
```

<210> SEQ ID NO 2
<211> LENGTH: 284
<212> TYPE: PRT
<213> ORGANISM: Phleum pratense

<400> SEQUENCE: 2

```
Ala Asp Leu Gly Tyr Gly Pro Ala Thr Pro Ala Ala Pro Ala Ala Gly
1               5                   10                  15

Tyr Thr Pro Ala Ala Pro Ala Gly Ala Glu Pro Ala Gly Lys Ala Thr
            20                  25                  30

Thr Glu Glu Gln Lys Leu Ile Glu Lys Ile Asn Ala Gly Phe Lys Ala
        35                  40                  45

Ala Leu Ala Ala Ala Ala Gly Val Pro Pro Ala Asp Lys Tyr Arg Thr
    50                  55                  60

Phe Val Ala Thr Phe Gly Ala Ala Ser Asn Lys Ala Phe Ala Glu Gly
65                  70                  75                  80

Leu Ser Gly Glu Pro Lys Gly Ala Ala Glu Ser Ser Ser Lys Ala Ala
                85                  90                  95

Leu Thr Ser Lys Leu Asp Ala Ala Tyr Lys Leu Ala Tyr Lys Thr Ala
            100                 105                 110

Glu Gly Ala Thr Pro Glu Ala Lys Tyr Asp Ala Tyr Val Ala Thr Leu
        115                 120                 125

Ser Glu Ala Leu Arg Ile Ile Ala Gly Thr Leu Glu Val His Ala Val
    130                 135                 140

Lys Pro Ala Ala Glu Glu Val Lys Val Ile Pro Ala Gly Glu Leu Gln
145                 150                 155                 160

Val Ile Glu Lys Val Asp Ala Ala Phe Lys Val Ala Ala Thr Ala Ala
```

```
                165                 170                 175

Asn Ala Ala Pro Ala Asn Asp Lys Phe Thr Val Phe Glu Ala Ala Phe
            180                 185                 190

Asn Asn Ala Ile Lys Ala Ser Thr Gly Gly Ala Tyr Glu Ser Tyr Lys
        195                 200                 205

Phe Ile Pro Ala Leu Glu Ala Ala Val Lys Gln Ala Tyr Ala Ala Thr
    210                 215                 220

Val Ala Thr Ala Pro Glu Val Lys Tyr Thr Val Phe Glu Thr Ala Leu
225                 230                 235                 240

Lys Lys Ala Ile Thr Ala Met Ser Glu Ala Gln Lys Ala Ala Lys Pro
                245                 250                 255

Ala Ala Ala Ala Thr Ala Thr Ala Thr Ser Ala Val Gly Ala Ala Thr
            260                 265                 270

Gly Ala Ala Thr Ala Ala Thr Gly Gly Tyr Lys Val
        275                 280


<210> SEQ ID NO 3
<211> LENGTH: 795
<212> TYPE: DNA
<213> ORGANISM: Phleum pratense

<400> SEQUENCE: 3

gccgatctag gctacggccc ggccacccca gctgccccgg ccgccggcta cacccccgcc     60

gccccggccg gagcggagcc agcaggtaag gcgacgaccg aggagcagaa gctgatcgag    120

aagatcaacg ccggcttcaa ggcggccttg gccgctgccg ccggcgtccc gccagcggac    180

aagtacagga cgttcgtcgc aaccttcggc gcggcctcca acaaggcctt cgcggagggc    240

ctctcgggcg agcccaaggg cgccgccgaa tccagctccg gcgcgacgcc tgaggccaag    300

tacgacgcct acgtcgccac cctaagcgag gcgctccgca tcatcgccgg caccctcgag    360

gtccacgccg tcaagcccgc ggccgaggag gtcaaggtta tccctgccgg cgagctgcag    420

gtcatcgaga aggtcgacgc cgccttcaag gtcgctgcca ccgccgccaa cgccgcgccc    480

gccaacgaca agttcaccgt cttcgaggcc gccttcaaca acgccatcaa ggcgagcacg    540

ggcggcgcct acgagagcta caagttcatc cccgccctgg aggccgccgt caagcaggcc    600

tacgccgcca ccgtcgccac cgcgccggag gtcaagtaca ccgtctttga gaccgcgctg    660

aaaaaggcca tcaccgccat gtccgaggcc cagaaggctg ccaagcccgc tgccgctgcc    720

accgccaccg caacctccgc cgttggcgcg gccaccggcg ccgccaccgc cgctactggt    780

ggctacaaag tctga                                                     795


<210> SEQ ID NO 4
<211> LENGTH: 264
<212> TYPE: PRT
<213> ORGANISM: Phleum pratense

<400> SEQUENCE: 4

Ala Asp Leu Gly Tyr Gly Pro Ala Thr Pro Ala Ala Pro Ala Ala Gly
  1               5                  10                  15

Tyr Thr Pro Ala Ala Pro Ala Gly Ala Glu Pro Ala Gly Lys Ala Thr
             20                  25                  30

Thr Glu Glu Gln Lys Leu Ile Glu Lys Ile Asn Ala Gly Phe Lys Ala
         35                  40                  45

Ala Leu Ala Ala Ala Ala Gly Val Pro Pro Ala Asp Lys Tyr Arg Thr
     50                  55                  60
```

-continued

```
Phe Val Ala Thr Phe Gly Ala Ala Ser Asn Lys Ala Phe Ala Glu Gly
 65                  70                  75                  80

Leu Ser Gly Glu Pro Lys Gly Ala Ala Glu Ser Ser Ser Gly Ala Thr
                 85                  90                  95

Pro Glu Ala Lys Tyr Asp Ala Tyr Val Ala Thr Leu Ser Glu Ala Leu
            100                 105                 110

Arg Ile Ile Ala Gly Thr Leu Glu Val His Ala Val Lys Pro Ala Ala
        115                 120                 125

Glu Glu Val Lys Val Ile Pro Ala Gly Glu Leu Gln Val Ile Glu Lys
    130                 135                 140

Val Asp Ala Ala Phe Lys Val Ala Ala Thr Ala Ala Asn Ala Ala Pro
145                 150                 155                 160

Ala Asn Asp Lys Phe Thr Val Phe Glu Ala Ala Phe Asn Asn Ala Ile
                165                 170                 175

Lys Ala Ser Thr Gly Gly Ala Tyr Glu Ser Tyr Lys Phe Ile Pro Ala
            180                 185                 190

Leu Glu Ala Ala Val Lys Gln Ala Tyr Ala Ala Thr Val Ala Thr Ala
        195                 200                 205

Pro Glu Val Lys Tyr Thr Val Phe Glu Thr Ala Leu Lys Lys Ala Ile
    210                 215                 220

Thr Ala Met Ser Glu Ala Gln Lys Ala Ala Lys Pro Ala Ala Ala Ala
225                 230                 235                 240

Thr Ala Thr Ala Thr Ser Ala Val Gly Ala Ala Thr Gly Ala Ala Thr
                245                 250                 255

Ala Ala Thr Gly Gly Tyr Lys Val
            260
```

<210> SEQ ID NO 5
<211> LENGTH: 783
<212> TYPE: DNA
<213> ORGANISM: Phleum pratense

<400> SEQUENCE: 5

```
gccgatctag gctacggccc ggccacccca gctgccccgg ccgccggcta cacccccgcc     60

gccccggccg gagcggagcc agcaggtaag gcgacgaccg aggagcagaa gctgatcgag    120

aagatcaacg ccggcttcaa ggcggccttg gccgctgccg ccggcgtccc gccagcggac    180

aagtacagga cgttcgtcgc aaccttcggc gcggcctcca acaaggcctt cgcggagggc    240

ctctcgggcg agcccaaggg cgccgccgaa tccagctcca aggccgcgct cacctccaag    300

ctcgacgccg cctacaagct cgcctacaag acagccgagg gcgcgacgcc tgaggccaag    360

tacgacgcct acgtcgccac cctaagcgag gcgctccgca tcatcgccgg caccctcgag    420

gtccacgccg tcaagcccgc ggccgaggag gtcaaggtta tccctgccgg cgagctgcag    480

gtcatcgaga aggtcgacgc cgccttcaag gtcgctgcca ccagcacggg cggcgcctac    540

gagagctaca agttcatccc cgccctggag gccgccgtca agcaggccta cgccgccacc    600

gtcgccaccg cgccggaggt caagtacacc gtctttgaga ccgcgctgaa aaaggccatc    660

accgccatgt ccgaggccca gaaggctgcc aagcccgctg ccgctgccac cgccaccgca    720

acctccgccg ttggcgcggc caccggcgcc gccaccgccg ctactggtgg ctacaaagtc    780

tga                                                                  783
```

<210> SEQ ID NO 6
<211> LENGTH: 260
<212> TYPE: PRT

<213> ORGANISM: Phleum pratense

<400> SEQUENCE: 6

```
Ala Asp Leu Gly Tyr Gly Pro Ala Thr Pro Ala Ala Pro Ala Ala Gly
  1               5                  10                  15

Tyr Thr Pro Ala Ala Pro Ala Gly Ala Glu Pro Ala Gly Lys Ala Thr
             20                  25                  30

Thr Glu Glu Gln Lys Leu Ile Glu Lys Ile Asn Ala Gly Phe Lys Ala
         35                  40                  45

Ala Leu Ala Ala Ala Ala Gly Val Pro Pro Ala Asp Lys Tyr Arg Thr
     50                  55                  60

Phe Val Ala Thr Phe Gly Ala Ala Ser Asn Lys Ala Phe Ala Glu Gly
 65                  70                  75                  80

Leu Ser Gly Glu Pro Lys Gly Ala Ala Glu Ser Ser Ser Lys Ala Ala
                 85                  90                  95

Leu Thr Ser Lys Leu Asp Ala Ala Tyr Lys Leu Ala Tyr Lys Thr Ala
            100                 105                 110

Glu Gly Ala Thr Pro Glu Ala Lys Tyr Asp Ala Tyr Val Ala Thr Leu
        115                 120                 125

Ser Glu Ala Leu Arg Ile Ile Ala Gly Thr Leu Glu Val His Ala Val
    130                 135                 140

Lys Pro Ala Ala Glu Glu Val Lys Val Ile Pro Ala Gly Glu Leu Gln
145                 150                 155                 160

Val Ile Glu Lys Val Asp Ala Ala Phe Lys Val Ala Ala Thr Ser Thr
                165                 170                 175

Gly Gly Ala Tyr Glu Ser Tyr Lys Phe Ile Pro Ala Leu Glu Ala Ala
            180                 185                 190

Val Lys Gln Ala Tyr Ala Ala Thr Val Ala Thr Ala Pro Glu Val Lys
        195                 200                 205

Tyr Thr Val Phe Glu Thr Ala Leu Lys Lys Ala Ile Thr Ala Met Ser
    210                 215                 220

Glu Ala Gln Lys Ala Ala Lys Pro Ala Ala Ala Ala Thr Ala Thr Ala
225                 230                 235                 240

Thr Ser Ala Val Gly Ala Ala Thr Gly Ala Ala Thr Ala Ala Thr Gly
                245                 250                 255

Gly Tyr Lys Val
            260
```

<210> SEQ ID NO 7
<211> LENGTH: 723
<212> TYPE: DNA
<213> ORGANISM: Phleum pratense

<400> SEQUENCE: 7

```
gccgatctag gctacggccc ggccaccccca gctgccccgg ccgccggcta cacccccgcc      60

gccccggccg gagcggagcc agcaggtaag gcgacgaccg aggagcagaa gctgatcgag     120

aagatcaacg ccggcttcaa ggcggccttg gccgctgccg ccggcgtccc gccagcggac     180

aagtacagga cgttcgtcgc aaccttcggc gcggcctcca acaaggcctt cgcggagggc     240

ctctcgggcg agcccaaggg cgccgccgaa tccagctccg gcgcgacgcc tgaggccaag     300

tacgacgcct acgtcgccac cctaagcgag gcgctccgca tcatcgccgg caccctcgag     360

gtccacgccg tcaagcccgc ggccgaggag gtcaaggtta tccctgccgg cgagctgcag     420

gtcatcgaga aggtcgacgc cgccttcaag gtcgctgcca ccagcacggg cggcgcctac     480
```

-continued

```
gagagctaca agttcatccc cgccctggag gccgccgtca agcaggccta cgccgccacc    540

gtcgccaccg cgccggaggt caagtacacc gtctttgaga ccgcgctgaa aaaggccatc    600

accgccatgt ccgaggccca gaaggctgcc aagcccgctg ccgctgccac cgccaccgca    660

acctccgccg ttggcgcggc caccggcgcc gccaccgccg ctactggtgg ctacaaagtc    720

tga                                                                  723


<210> SEQ ID NO 8
<211> LENGTH: 240
<212> TYPE: PRT
<213> ORGANISM: Phleum pratense

<400> SEQUENCE: 8

Ala Asp Leu Gly Tyr Gly Pro Ala Thr Pro Ala Ala Pro Ala Ala Gly
  1               5                  10                  15

Tyr Thr Pro Ala Ala Pro Ala Gly Ala Glu Pro Ala Gly Lys Ala Thr
             20                  25                  30

Thr Glu Glu Gln Lys Leu Ile Glu Lys Ile Asn Ala Gly Phe Lys Ala
         35                  40                  45

Ala Leu Ala Ala Ala Ala Gly Val Pro Pro Ala Asp Lys Tyr Arg Thr
     50                  55                  60

Phe Val Ala Thr Phe Gly Ala Ala Ser Asn Lys Ala Phe Ala Glu Gly
 65                  70                  75                  80

Leu Ser Gly Glu Pro Lys Gly Ala Ala Glu Ser Ser Ser Gly Ala Thr
                 85                  90                  95

Pro Glu Ala Lys Tyr Asp Ala Tyr Val Ala Thr Leu Ser Glu Ala Leu
            100                 105                 110

Arg Ile Ile Ala Gly Thr Leu Glu Val His Ala Val Lys Pro Ala Ala
        115                 120                 125

Glu Glu Val Lys Val Ile Pro Ala Gly Glu Leu Gln Val Ile Glu Lys
    130                 135                 140

Val Asp Ala Ala Phe Lys Val Ala Ala Thr Ser Thr Gly Gly Ala Tyr
145                 150                 155                 160

Glu Ser Tyr Lys Phe Ile Pro Ala Leu Glu Ala Ala Val Lys Gln Ala
                165                 170                 175

Tyr Ala Ala Thr Val Ala Thr Ala Pro Glu Val Lys Tyr Thr Val Phe
            180                 185                 190

Glu Thr Ala Leu Lys Lys Ala Ile Thr Ala Met Ser Glu Ala Gln Lys
        195                 200                 205

Ala Ala Lys Pro Ala Ala Ala Ala Thr Ala Thr Ala Thr Ser Ala Val
    210                 215                 220

Gly Ala Ala Thr Gly Ala Ala Thr Ala Ala Thr Gly Gly Tyr Lys Val
225                 230                 235                 240


<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

gccgatctag gctacggccc ggcc                                            24


<210> SEQ ID NO 10
<211> LENGTH: 36
```

-continued

<212> TYPE: DNA
<213> ORGANISM: Artificial Sequence
<220> FEATURE:
<223> OTHER INFORMATION: Description of Artificial Sequence: Synthetic primer

<400> SEQUENCE: 10
aacataacta gtggcagcga ccttgaaggc ggcgtc 36

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
atctaactag tacgggcggc gcctacgaga 30

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
aacataaagc tttcagactt tgtagccacc agt 33

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ggagctggat tcggcggcgc ccttggg 27

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
gccgccgaat ccagctccgg cgcgacgcct gaggccaagt acgac 45

<210> SEQ ID NO 15
<211> LENGTH: 375
<212> TYPE: DNA
<213> ORGANISM: Poa pratensis

<400> SEQUENCE: 15
gccgccgtag acagctccaa ggccgcgctc acctccaagc tcgacgccgc ctacaagctc 60
gcctacaagt cagccgaggg cgcgacgccc gaggctaagt acgacgacta cgtcgccacc 120
cttagcgagg ccctccgcat cattgccggc accctcgagg tccacggcgt caagcccgcg 180
gccgaggagg tcaaggccac ccccgccggc gagctccagg tcatcgacaa ggtcgacgcc 240
gccttcaagg tcgctgccac cgccgccaac gccgcccccg ccaacgacaa gttcaccgtc 300
ttcgaggccg ccttcaacga tgccatcaag gcgagcacgg gcggcgccta ccagagctac 360
aagttcatcc ccgcc 375

<210> SEQ ID NO 16
<211> LENGTH: 382
<212> TYPE: DNA
<213> ORGANISM: Lolium perenne

<400> SEQUENCE: 16
ggctacgccg atcaaagcaa gaaccagctc acctccaagc tcgacgccgc cttaaagcct 60
cgcttacgag gctgcccagg gcgccactcc cgaggccaag tacgatgcct acgtcgccac 120
cctcaccgag gcgctccgcg tcatcgccgg caccctcgag gtccacgccg taaagcccgc 180
cgccgaggag gtcaaggtcg gcgccatccc cgccgccgag gtgcagctca tcgacaaggt 240
cgacgccgcg tacaggaccg ccgccactgc cgccaacgcc gcccccgcca acgacaagtt 300
caccgtcttc gagaacacct ttaacaatgc catcaaggtg agcctgggcg ccgcctacga 360
cagctacaag ttcatcccca cc 382

<210> SEQ ID NO 17
<211> LENGTH: 378
<212> TYPE: DNA
<213> ORGANISM: Hordeum vulgare

<400> SEQUENCE: 17
gatcgccggc cagtccagct ccatggccaa actctccagc agcctcgaac tctcctacaa 60
gctcgcctac gacaaagccc agggcgccac cccgaggcca agtacgacgc ctacgtcgcc 120
accctcaccg agtcgctccg cgtcatctcc ggcaccctcg aggtccactc cgtcaagccc 180
gccgccgagg aggttaaggg cgtccccgcc ggcgagctga aggccattga ccaggtcgac 240
gccgccttca ggaccgccgc caccgccgct gacgctgccc cggccaacga caagttcacc 300
gtcttcgagt cgcttcaaca aggtccatca aggaaaccac ggggcggcgc gtacgagagt 360
tacaagttca tccccgcc 378

<210> SEQ ID NO 18
<211> LENGTH: 379
<212> TYPE: DNA
<213> ORGANISM: Triticum aestivum

<400> SEQUENCE: 18
gatgcccgcc cagtcagcct ccatggcatc actctccaag agcctcgaag cctcctacaa 60
gctcgcctac gacaaagccc agggcgccac ccccgagacc aagtacgaca cctacgtcgc 120
cagtctcacc gagtcgctcc gcgtcatctc cggcgccttc gaggtccact ccgtcaagcc 180
cgccgccgag gaggtcaagg ggatccccgc cccccagctc aagaccatcg accagatcga 240
cgccgcctac aggaccgccg ccaccgccgc cgacgctgcc ccggtcaacg acaagttcac 300
cgtcttcgag tccgccttca acaaggccat caaggagacc acgggcggcg catacgacaa 360
ctacaagttc gtccccgcc 379

<210> SEQ ID NO 19
<211> LENGTH: 206
<212> TYPE: PRT
<213> ORGANISM: Poa pratensis

<400> SEQUENCE: 19

-continued

```
Pro Ala Ala Asn Lys Tyr Lys Thr Phe Val Ala Thr Phe Gly Ala Ala
  1               5                  10                  15

Ser Asn Lys Ala Phe Ala Glu Ala Leu Ser Thr Glu Pro Lys Gly Ala
                 20                  25                  30

Ala Val Asp Ser Ser Lys Ala Ala Leu Thr Ser Lys Leu Asp Ala Ala
         35                  40                  45

Tyr Lys Leu Ala Tyr Lys Ser Ala Glu Gly Ala Thr Pro Glu Ala Lys
     50                  55                  60

Tyr Asp Asp Tyr Val Ala Thr Leu Ser Glu Ala Leu Arg Ile Ile Ala
 65                  70                  75                  80

Gly Thr Leu Glu Val His Gly Val Lys Pro Ala Ala Glu Glu Val Lys
                 85                  90                  95

Ala Thr Pro Ala Gly Glu Leu Gln Val Ile Asp Lys Val Asp Ala Ala
            100                 105                 110

Phe Lys Val Ala Ala Thr Ala Ala Asn Ala Ala Pro Ala Asn Asp Lys
        115                 120                 125

Phe Thr Val Phe Glu Ala Ala Phe Asn Asp Ala Ile Lys Ala Ser Thr
    130                 135                 140

Gly Gly Ala Tyr Gln Ser Tyr Lys Phe Ile Pro Ala Leu Glu Ala Ala
145                 150                 155                 160

Val Lys Gln Ser Tyr Ala Ala Thr Val Ala Thr Ala Pro Ala Val Lys
                165                 170                 175

Tyr Thr Val Phe Glu Thr Ala Leu Lys Lys Ala Ile Thr Ala Met Ser
            180                 185                 190

Gln Ala Gln Lys Ala Ala Lys Pro Ala Ala Ala Ala Thr Gly
        195                 200                 205


<210> SEQ ID NO 20
<211> LENGTH: 204
<212> TYPE: PRT
<213> ORGANISM: Lolium perenne

<400> SEQUENCE: 20

Pro Pro Ala Asp Lys Tyr Lys Thr Phe Val Glu Thr Phe Gly Thr Ala
  1               5                  10                  15

Thr Asn Lys Ala Phe Val Glu Gly Leu Ala Ser Gly Tyr Ala Asp Gln
                 20                  25                  30

Ser Lys Asn Gln Leu Thr Ser Lys Leu Asp Ala Ala Leu Lys Leu Ala
         35                  40                  45

Tyr Glu Ala Ala Gln Gly Ala Thr Pro Glu Ala Lys Tyr Asp Ala Tyr
     50                  55                  60

Val Ala Thr Leu Thr Glu Ala Leu Arg Val Ile Ala Gly Thr Leu Glu
 65                  70                  75                  80

Val His Ala Val Lys Pro Ala Ala Glu Glu Val Lys Val Gly Ala Ile
                 85                  90                  95

Pro Ala Ala Glu Val Gln Leu Ile Asp Lys Val Asp Ala Ala Tyr Arg
            100                 105                 110

Thr Ala Ala Thr Ala Ala Asn Ala Ala Pro Ala Asn Asp Lys Phe Thr
        115                 120                 125

Val Phe Glu Asn Thr Phe Asn Asn Ala Ile Lys Val Ser Leu Gly Ala
    130                 135                 140

Ala Tyr Asp Ser Tyr Lys Phe Ile Pro Thr Leu Val Ala Ala Val Lys
145                 150                 155                 160

Gln Ala Tyr Ala Ala Lys Gln Ala Thr Ala Pro Glu Val Lys Tyr Thr
                165                 170                 175
```

```
Val Ser Glu Thr Ala Leu Lys Lys Ala Val Thr Ala Met Ser Glu Ala
            180                 185                 190

Glu Lys Glu Ala Thr Pro Ala Ala Ala Ala Thr Ala
        195                 200


<210> SEQ ID NO 21
<211> LENGTH: 208
<212> TYPE: PRT
<213> ORGANISM: Hordeum vulgare

<400> SEQUENCE: 21

Pro Pro Ala Asp Lys Tyr Lys Thr Phe Glu Ala Thr Phe Ala Ala Ala
  1               5                  10                  15

Ser Asn Lys Ala Phe Ala Glu Val Leu Lys Gly Ala Ala Thr Gly Gln
             20                  25                  30

Ile Ala Gly Gln Ser Ser Ser Met Ala Lys Leu Ser Ser Ser Leu Glu
         35                  40                  45

Leu Ser Tyr Lys Leu Ala Tyr Asp Lys Ala Gln Gly Ala Thr Pro Glu
     50                  55                  60

Ala Lys Tyr Asp Ala Tyr Val Ala Thr Leu Thr Glu Ser Leu Arg Val
 65                  70                  75                  80

Ile Ser Gly Thr Leu Glu Val His Ser Val Lys Pro Ala Ala Glu Glu
                 85                  90                  95

Val Lys Gly Val Pro Ala Gly Glu Leu Lys Ala Ile Asp Gln Val Asp
            100                 105                 110

Ala Ala Phe Arg Thr Ala Ala Thr Ala Ala Asp Ala Ala Pro Ala Asn
        115                 120                 125

Asp Lys Phe Thr Val Phe Glu Ser Leu Gln Gln Gly Pro Ser Arg Lys
    130                 135                 140

Pro Arg Gly Gly Ala Tyr Glu Ser Tyr Lys Phe Ile Pro Ala Leu Glu
145                 150                 155                 160

Ala Ala Val Lys Gln Ala Tyr Ala Ala Thr Val Ala Ala Ala Pro Glu
                165                 170                 175

Val Lys Phe Thr Val Phe Gln Thr Ala Leu Ser Lys Ala Ile Asn Ala
            180                 185                 190

Met Thr Gln Ala Gly Lys Val Ala Lys Pro Ala Ala Ala Ala Thr Ala
        195                 200                 205


<210> SEQ ID NO 22
<211> LENGTH: 210
<212> TYPE: PRT
<213> ORGANISM: Triticum aestivum
<220> FEATURE:
<221> NAME/KEY: MOD_RES
<222> LOCATION: (19)
<223> OTHER INFORMATION: Variable amino acid
<220> FEATURE:
<221> NAME/KEY: MOD_RES
<222> LOCATION: (100)..(101)
<223> OTHER INFORMATION: Variable amino acid

<400> SEQUENCE: 22

Pro Pro Ala Asp Lys Tyr Lys Thr Phe Glu Ala Thr Phe Ser Ala Ala
  1               5                  10                  15

Ser Asn Xaa Ala Phe Ala Asp Val Leu Lys Ala Ala Ala Ser Gly Gln
             20                  25                  30

Met Pro Ala Gln Ser Ala Ser Met Ala Ser Leu Ser Lys Ser Leu Glu
         35                  40                  45
```

-continued

```
Ala Ser Tyr Lys Leu Ala Tyr Asp Lys Ala Gln Gly Ala Thr Pro Glu
    50                  55                  60

Thr Lys Tyr Asp Thr Tyr Val Ala Ser Leu Thr Glu Ser Leu Arg Val
65                  70                  75                  80

Ile Ser Gly Ala Phe Glu Val His Ser Val Lys Pro Ala Ala Glu Glu
                85                  90                  95

Val Lys Gly Xaa Xaa Ile Pro Ala Pro Gln Leu Lys Thr Ile Asp Gln
            100                 105                 110

Ile Asp Ala Ala Tyr Arg Thr Ala Ala Thr Ala Ala Asp Ala Ala Pro
        115                 120                 125

Val Asn Asp Lys Phe Thr Val Phe Glu Ser Ala Phe Asn Lys Ala Ile
    130                 135                 140

Lys Glu Thr Thr Gly Gly Ala Tyr Asp Asn Tyr Lys Phe Val Pro Ala
145                 150                 155                 160

Leu Glu Ser Ala Val Lys Gln Ala Tyr Ala Ala Thr Val Ala Ser Ala
                165                 170                 175

Pro Glu Val Lys Tyr Ala Val Phe Gln Ala Ala Leu Ser Lys Ala Ile
            180                 185                 190

Asn Ala Met Val Glu Ala Glu Lys Asp Ala Gly Ala Ala Ala Ala Gly
        195                 200                 205

Gly Tyr
    210
```

PHL P 5A DERIVATIVES HAVING REDUCED ALLERGENEITY AND RETAINED T-CELL REACTIVITY

The present invention relates to the preparation and use of variants of the group 5 allergen of the Pooideae which are characterised by reduced IgE reactivity compared with the known wild-type allergens and at the same time by substantially retained reactivity with T lymphocytes.

These hypoallergenic allergen variants can be employed for the specific immunotherapy (hyposensitisation) of patients having grass pollen allergy or for the preventative immunotherapy of grass pollen allergies.

A preferred embodiment of the invention relates to variants of the major allergen Phl p 5a from the pollen of timothy grass (*Phleum pretense*).

BACKGROUND OF THE INVENTION

Type 1 allergies are of importance worldwide. Up to 20% of the population in industrialised countries suffer from complaints such as allergic rhinitis, conjunctivitis or bronchial asthma. These allergies are caused by allergens present in the air (aeroallergens) which are liberated from sources of various origin, such as plant pollen, mites, cats or dogs. Up to 40% of these type 1 allergy sufferers in turn exhibit specific IgE reactivity with grass pollen allergens (Freidhoff et al., 1986, J. Allergy Clin. Immunol. 78, 1190-2002).

The substances which trigger type 1 allergy are proteins, glycoproteins or polypeptides. After uptake via the mucous membranes, these allergens react with the IgE molecules bonded to the surface of mast cells in sensitised individuals. If two IgE molecules are crosslinked to one another by an allergen, this results in the release of mediators (for example histamine, prostaglandins) and cytokines by the effector cell and thus in the corresponding clinical symptoms.

A distinction is made between major and minor allergens depending on the relative frequency with which the individual allergen molecules react with the IgE antibodies of allergy sufferers.

In the case of timothy grass (*Phleum pretense*), Phl p 1 (Petersen et al., 1993, J. Allergy Clin. Immunol. 92: 789-796), Phl p 5 (Matthiesen and Löwenstein, 1991, Clin. Exp. Allergy 21: 297-307; Petersen et al., 1992, Int. Arch. Allergy Immunol. 98: 105-109), Phl p 6 (Petersen et al., 1995, Int. Arch. Allergy Immunol. 108, 49-54). Phl p 2/3 (Dolecek et al., 1993, FEBS 335 (3), 299-304), Phl p 4 (Haavik et al., 1985, Int. Arch. Allergy Appl. Immunol. 78: 260-268; Valenta et al., 1992, Int. Arch. Allergy Immunol. 97: 287-294, Fischer et al., 1996, J. Allergy Clin. Immunol. 98: 189-198) and Phl p 13 (Suck et al., 2000, Clin. Exp. Allergy 30: 324-332; Suck et al., 2000, Clin. Exp. Allergy 30: 1395-1402) have hitherto been identified as major allergens.

The dominant major allergens of timothy grass (*Phleum pretense*) are Phl p 1 and Phl p 5, with Phl p 5 occurring in two forms 5a and 5b which differ in respect of their molecular weight and are encoded by independent genes. The deduced amino acid sequences both of Phl p 5a and also of Phl p 5b have been determined by means of the recombinant DNA technique. Phl p 5a is a protein of about 32 kDa and reacts with the IgE antibodies of 85-90% of grass pollen allergy sufferers. Phl p 5a exists in a series of homologous variants which differ from one another through point mutations and probably correspond to different allelic forms. The pollen of related grass species, such as, for example, *Lolium perenne, Poa pratensis* inter alia, contains allergens which are homologous with that of Phl p 5a and together are known as group 5 allergens. The high structural homology of these group 5 allergens of grass species causes correspondingly high cross reactivity of the molecules with the IgE antibodies of grass pollen allergy sufferers.

A classical approach to effective therapeutic treatment of allergies is specific immunotherapy or hyposensitisation (Fiebig, 1995, Allergo J. 4 (6): 336-339, Bousquet et al., 1998, J. Allergy Clin. Immunol. 102 (4): 558-562). In this method, the patient is injected subcutaneously with natural allergen extracts in increasing doses. However, there is a risk in this method of allergic reactions or even anaphylactic shock. In order to minimise these risks, innovative preparations in the form of allergoids are employed. These are chemically modified allergen extracts which have significantly reduced IgE reactivity, but identical T-cell reactivity compared with the untreated extract (Fiebig, 1995, Allergo J. 4 (7): 377-382).

Even more substantial therapy optimisation would be possible with allergens prepared by recombinant methods. Defined cocktails of high-purity allergens prepared by recombinant methods, optionally matched to the individual sensitisation patterns of the patients, could replace extracts from natural allergen sources since these, in addition to the various allergens, contain a relatively large number of immunogenic, but non-allergenic secondary proteins.

Realistic perspectives which may result in reliable hyposensitisation with recombinant expression products are offered by specifically mutated recombinant allergens in which IgE epitopes are specifically deleted without impairing the T-cell epitopes which are essential for therapy (Schramm et al., 1999, J. Immunol. 162: 2406-2414).

A further possibility for therapeutic influencing of the disturbed T helper cell equilibrium in allergy sufferers is treatment with expressible DNA which encodes for the relevant allergens (immunotherapeutic DNA vaccination). Initial experimental evidence of allergen-specific influencing of the immune response by a DNA vaccine of this type has been furnished in rodents by injection of allergen-encoding DNA (Hsu et al., 1996, Nature Medicine 2 (5): 540-544).

The object on which the present invention is based consisted in the provision of novel variants of the group 5 allergens of the Pooideae at the protein and DNA level which are distinguished by reduced IgE activity at the same time as substantial retention of the T-cell reactivity and are therefore suitable for specific immunotherapy and immunotherapeutic DNA vaccination.

BRIEF DESCRIPTION OF THE DRAWINGS

FIG. 1 shows sequence alignment of relevant regions of Phl p 5a-homologous cDNA sequences of Pooideae species: *Lolium perenne* (Lol p), *Poe pratensis* (Poa p) *Triticum aestivum* (Tri a) and *Hordeum vulgare* (Hor v). The numbering represents nucleotide positions of the DNA insertions.

FIG. 2A and FIG. 2B together show sequence alignment of Phl p 5a-homologous amino acid sequences (relevant sequence regions, deduced from DNA sequences) of Pooideae species: *Lolium perenne* (Lol p), *Poe pratensis* (Poa p) *Triticum aestivum* (Tri a) and *Hordeum vulgare* (Hor v). The numbering represents nucleotide positions of the DNA insertions.

FIGURES

FIG. 1: Alignment of relevant regions of Phl p 5a-homologous cDNA sequences of Pooideae species: *Lolium perenne* (Lol p), *Poa pratensis* (Poa p) *Triticum aestivum* (Tri a) and *Hordeum vulgatre* (Hor v)

Numbering: nucleotide positions of the DNA insertions

Phl p 5a, Poa p 5 and Lol p 5 sequences: cDNA sequences from "GenBank" database of the National Center for Biotechnology Information (NCBI), Bethesda, USA Hor v and Tri a sequences: EST sequences from EST database of the institute for Genomic Research (TIGR), Rockville, USA Black borders: sequence identity with Phl p 5a (based on GenBank AJ555152)

Dotted borders: deletion corresponding to amino acids 94-113 (based on GenBank AJ555152)

Dashed borders: deletion corresponding to amino acids 175-198 (based on GenBank AJ555152)

FIG. 2: Alignment of Phl p 5a-homologous amino acid sequences (relevant sequence regions, deduced from DNA sequences) of Pooideae species: *Lolium perenne* (Lol p), *Poa pratensis* (Poa p) *Triticum aestivum* (Tri a) and *Hordeum vulgare* (Hor v)

Numbering: nucleotide positions of the DNA insertions

Phl p 5a, Poa p 5 and Lol p 5 sequences: cDNA sequences from "GenBank" database of the National Center for Biotechnology Information (NCBI), Bethesda, USA Hor v and Tri a sequences: EST sequences from EST database of the Institute for Genomic Research (TIGR), Rockville, USA Black borders: sequence identity with Phl p 5a (based on GenBank AJ555152)

Dotted borders: deletion corresponding to amino acids 94-113 (based on GenBank AJ555152)

Dashed borders: deletion corresponding to amino acids 175-198 (based on GenBank AJ555152)

Figure 3:
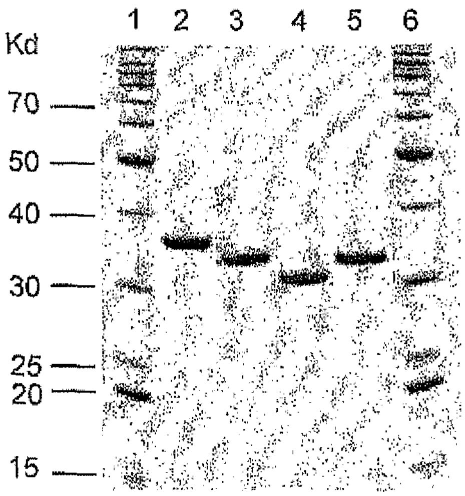
FIG. 3 shows SDS-PAGE of purified deletion mutants in the form of histidine fusion proteins. Lanes represent the follows: (1) marker; (2) rPhl p 5a wt (His); (3) Phl p 5a DM-Δ94-113 (His); (4) Phl p 5a DM-Δ94-113, 175-198 (His); (5) Phl p 5a DM-Δ75-198 (His); (6) Marker

FIG. 3: SDS-PAGE of purified deletion mutants in the form of histidine fusion proteins 1) Marker
2) rPhl p 5a wt (His)
3) Phl p 5a DM-Δ94-113 (His)
4) Phl p 5a DM-Δ94-113, 175-198 (His)
5) Phl p 5a DM-Δ175-198 (His)
6) Marker FIG. 4: SDS-PAGE of the purified non-fusion proteins Phl p 5a DM-D94-113, 175-198 and rPhl p 5a wt (top) and identity test with αPhl p 5 antibodies (bottom)

αPhl p 5 mAb Apha-1D11 binds region 175-198 (only rPhl p 5a wt is positive)

αPhl p 5a mAb Apha-3B2 binds a joint epitope of the two Phl p 5a molecules (both proteins positive)

(mAb: monoclonal antibody)

Figure 5:
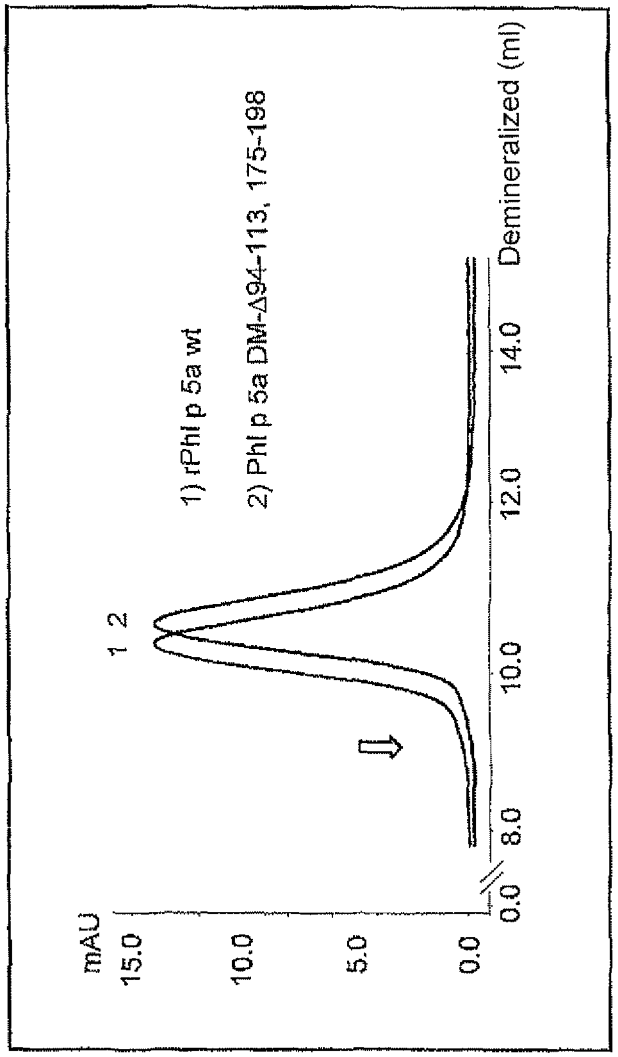
FIG. 5 shows analytical SEC of deletion mutant Phl p 5a DM-Δ94-113, 175-198 and of recombinant wild type Phl p 5a (purified non-fusion proteins)

FIG. 5: Analytical SEC of deletion mutant Phl p 5a DM-Δ94-113, 175-198 and of recombinant wild type Phl p 5a (purified non-fusion proteins)

Column: Superdex 75 HR101 30 (Amersham Biosciences, Uppsala, Sweden)

Eluent PBS

Arrow: exclusion volume

Figure 6:
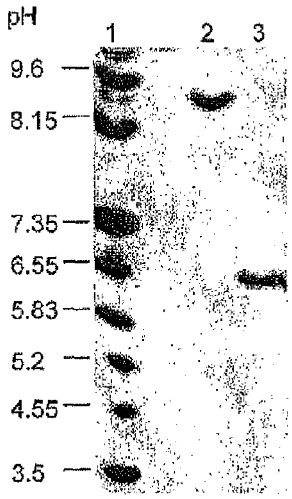
FIG. 6 shows results on non-denaturing isoelectric focusing of deletion mutant Phl p 5a DM-Δ94-113, 175-198 and of recombinant wild type Phl p 5a (purified non-fusion proteins). Lanes represent the follows: (1) IEF marker; (2) rPhl p 5a wt; (3) Phl p 5a DM-Δ94-113, 175-198

FIG. 6: Non-denaturing isoelectric focusing of deletion mutant Phl p 5a DM-Δ94-113, 175-198 and of recombinant wild type Phl p 5a (purified non-fusion proteins)

1) IEF marker
2) rPhl p 5a wt
3) Phl p 5a DM-Δ94-113, 175-198 pI rPhl p 5a wt=8.7 pI rPhl p 5a DM-Δ94-113, 175-198=6.4

Figure 7:
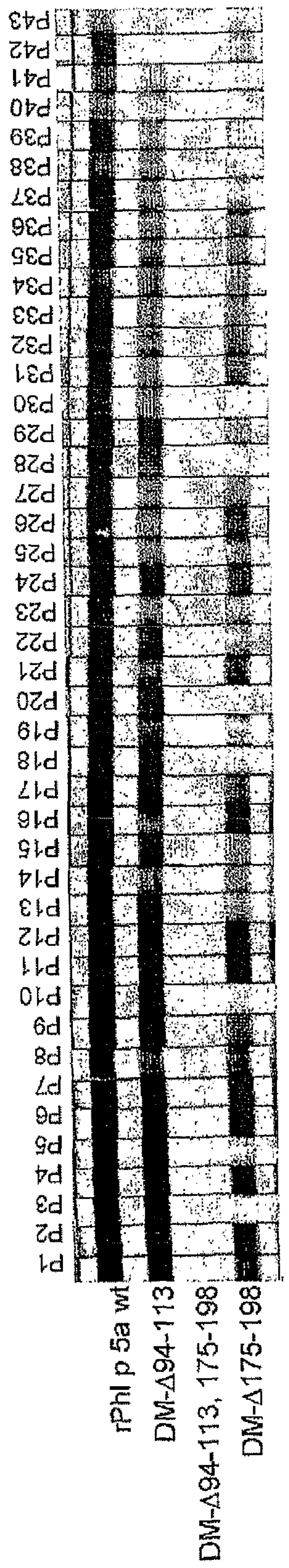
FIG. 7 shows results on strip test for checking the IgE binding ability of Phl p 5a deletion mutants (non-denaturing). Abbreviation: P is sera of clinically defined grass pollen allergy sufferers.

FIG. 7: Strip test for checking the IgE binding ability of Phl p 5a deletion mutants (non-denaturing)

P: sera of clinically defined grass pollen allergy sufferers

Figure 8:
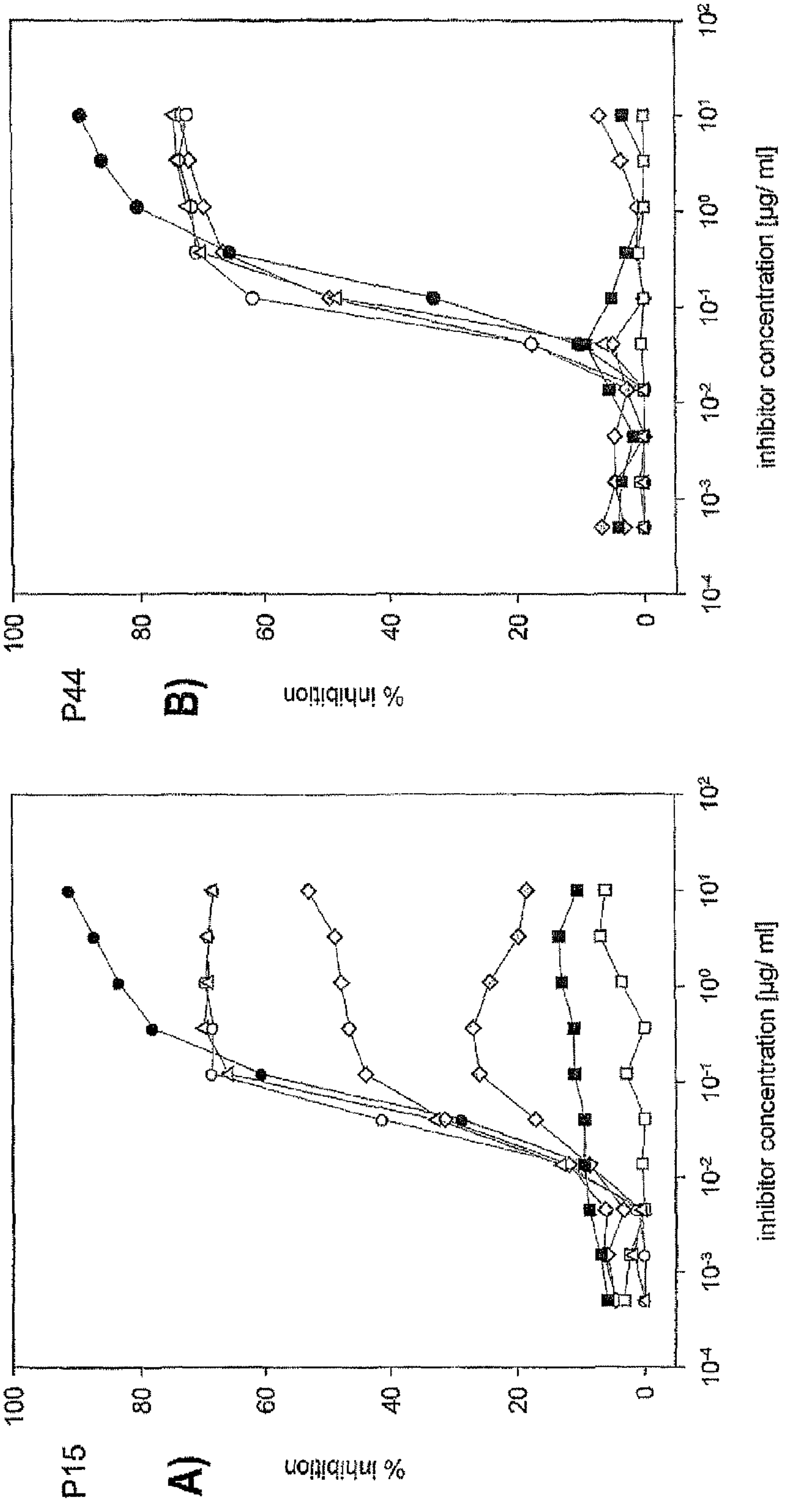
FIG. 8 shows determination of the reduced IgE reactivity of Phl p 5a deletion mutants by means of the EAST inhibition test with two representative single sera (a) and (b) and a serum pool (c). Abbreviation: P is sera of clinically defined grass pollen allergy sufferers.
Figure 8:
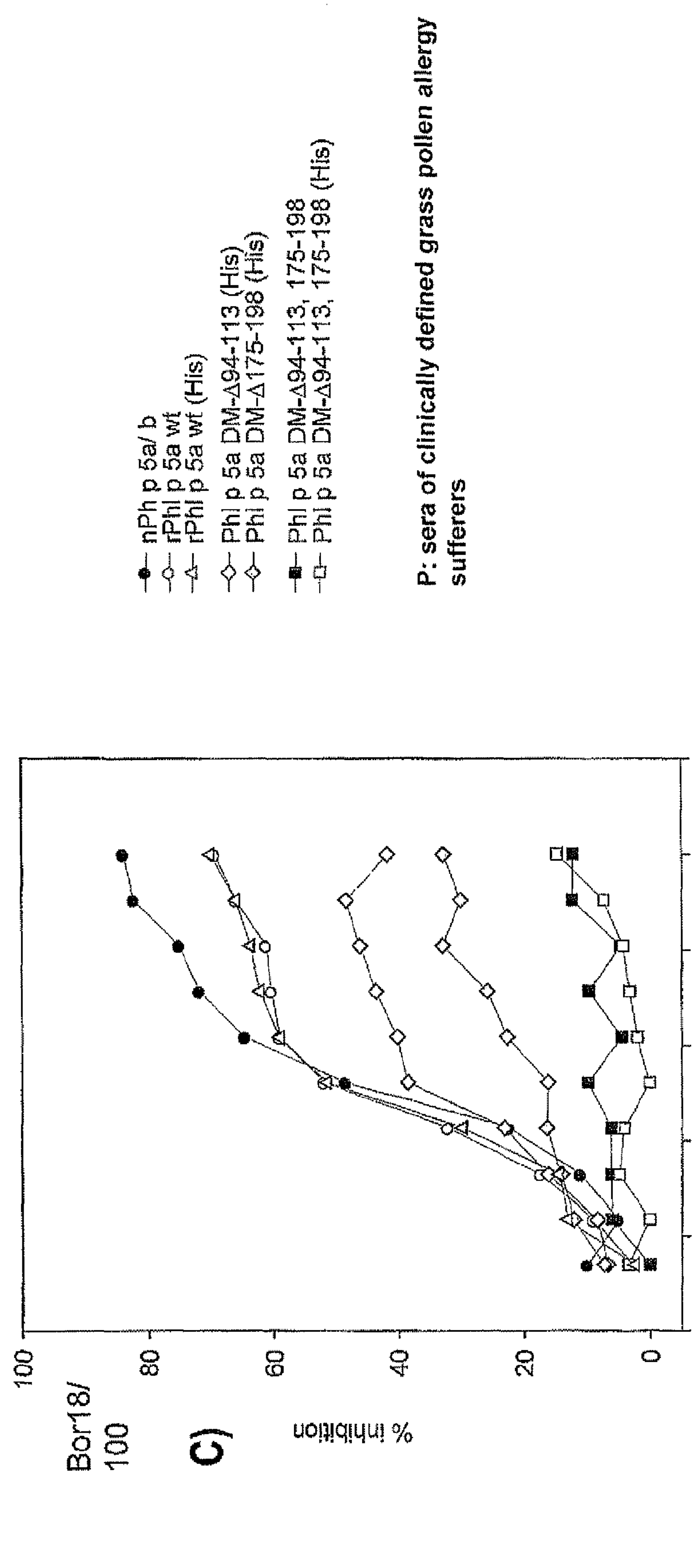

FIG. 8: Determination of the reduced IgE reactivity of Phl p 5a deletion mutants by means of the EAST inhibition test with two representative single sera (a and b) and a serum pool (c)

—●— nPh p 5a/b
—○— rPhl p 5a wt
—△— rPhl p 5a wt (His)
—◇— Phl p 5a DM-Δ94-113 (His)
—◈— Phl p 5a DM-Δ175-198 (His)
—■— Phl p 5a DM-Δ94-113, 175-198
—□— Phl p 5a DM-Δ94-113, 175-198 (His)

P: sera of clinically defined grass pollen allergy sufferers

Figure 9:
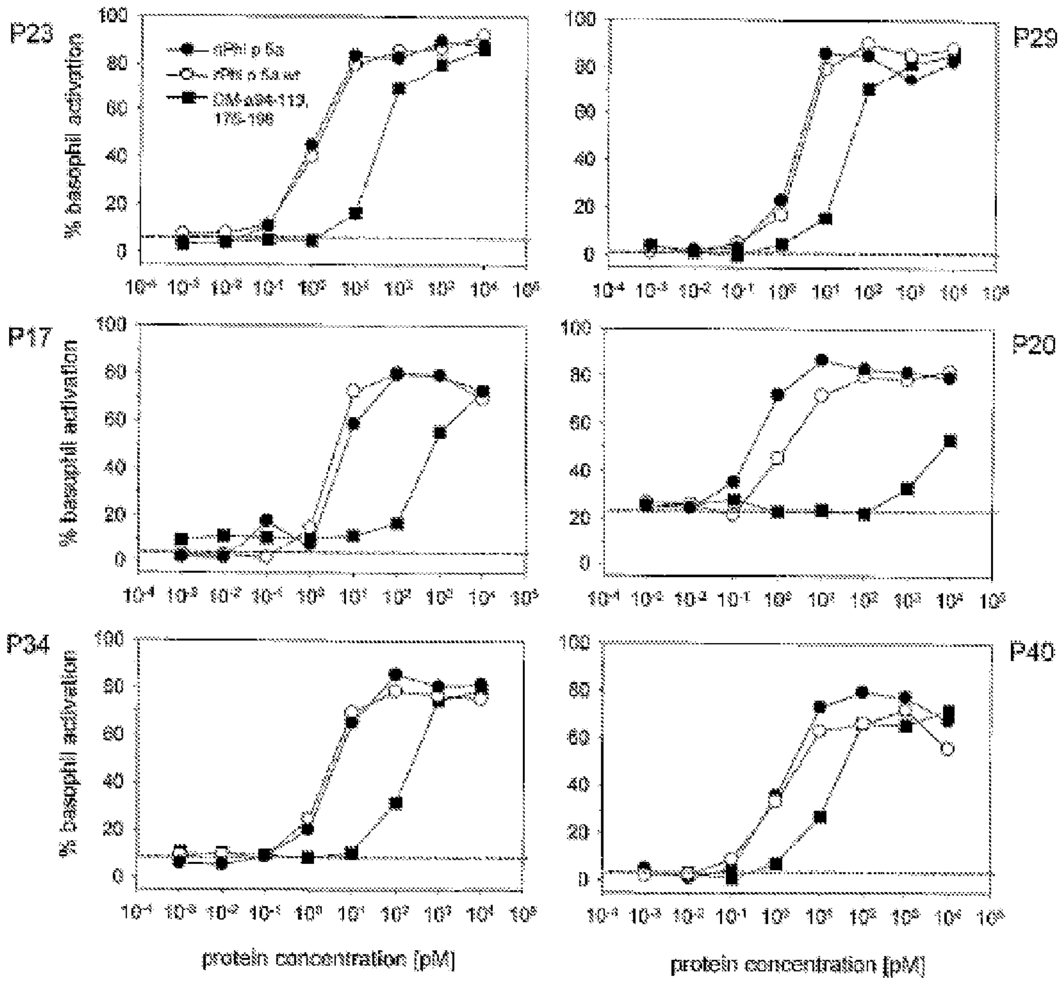
FIG. 9 shows determination of the hypoallergeneity of Phl p 5a deletion mutant Phl p 5a DM-Δ94-113, 175-198 by means of the basophil activation test with basophils of six different grass pollen allergy sufferers (P).

FIG. 9: Determination of the hypoallergeneity of Phl p 5a deletion mutant Phl p 5a DM-Δ94-113, 175-198 by means of the basophil activation test with basophils of six different grass pollen allergy sufferers (P)

DETAILED DESCRIPTION OF THE INVENTION

Mutagenesis and Cloning of cDNA Sequences

The starting point for the—particularly preferred in accordance with the invention—hypoallergenic Phl p 5a variants is the cDNA of an isoform of wild-type Phl p 5a which has been isolated with the aid of specific primers by polymerase chain reaction (PCR) from the total cDNA of pollen of timothy grass (*Phleum pratense*) (NCBI (National Center for Biotechnology Information, Bethesda, USA) GenBank number AJ555152) (SEQ ID NO 1). The amino acid sequence as per SEQ ID NO 2 has been deduced from the cDNA sequence. Phl p 5a, which consists of 284 amino acids, was expressed cytosolically as soluble protein in *E. coli* and subsequently purified. This recombinant wild-type form of Phl p 5a (rPhl p 5a wt) reacts with monoclonal anti-Phl p 5 antibodies and with IgE antibodies of grass pollen allergy sufferers which have reactivity with natural purified Phl p 5a (nPhl p 5a).

Starting from the described cDNA of rPhl p 5a wt, a series of different deletion variants (deletion mutants) was prepared by restriction/ligation methods and PCR and ligated into the expression vector pProExHTa (Invitrogen, Carlsbad, USA). Sections with a length of 6 to 72 bp distributed over the entire sequence of the cDNA molecule were deleted, causing induction of corresponding deletions in the polypeptide chains of the proteins expressed in *E. coli.*

The deletion variants of Phl p 5a were investigated by immunoblot for their binding ability to IgE antibodies of a representative serum pool of grass pollen allergy sufferers.

In this method, surprisingly, two deletion variants of Phl p 5a (Phl p 5a DM-Δ94-113, deletion of amino acids 94-113 and Phl p 5a DM-Δ175-198, deletion of amino acids 175-198 of rPhl p 5a wt) were found, which have reduced binding of IgE antibodies (representative serum pool).

These two Phl p 5a deletions served as starting point for the construction of a double deletion mutant containing both effective deletions (Php p 5a DM—Δ94-113, 175-198).

The construction of Phl p 5a DM-Δ94-113, Phl p 5a DM-Δ175-198 and Phl p 5a DM-Δ94-113, 175-198 by genetic engineering methods and the biochemical and immunological characterisation thereof are described below.

For the construction of deletion variant Phl p 5a DM-Δ94-113 (SEQ ID NO 3, cDNA sequence (795 bp), and SEQ ID NO 4, amino acid sequence (264 aa)), firstly two fragments were prepared starting from the cDNA of rPhl p 5a wt. Fragment "F1-93", encoding for amino acids 1-93 of rPhl p 5a wt, was prepared by PCR with the aid of primers 1 and 5, and fragment "F114-284" was prepared with the aid of primers 4 and 6 (primer sequences see Table 1). Fragments "F1-93" and "F114-284" were employed as matrix in a further PCR using primers 1 and 4, which resulted in amplification of the complete cDNA encoding for deletion variant Phl p 5a DM-Δ94-113. The basis of the connection of fragments "F1-93" and "F114-284" by PCR was a sequence region common to both fragments. This sequence region was formed by amplification of fragment "F114-284" by PCR by means of a particular sense oligonucleotide which contained an additional DNA sequence encoding for amino acids 88-93 in the 5' region (Table 1).

The cDNA sequence encoding for deletion variant Phl p 5a DM-Δ175-198 (SEQ ID NO 5, cDNA sequence (783 bp), and SEQ ID NO 6, amino acid sequence (260 aa)) was generated by restriction and subsequent ligation of two separately prepared cDNA fragments. The 5'-terminal fragment "F1-174" was prepared by PCR with the aid of primers 1 and 2 and the 3'-terminal fragment "F199-284" with the aid of primers 3 and 4. The cDNA fragments were digested with the restriction enzyme SpeI and subsequently ligated (see Table 1). The ligation product was amplified by PCR using primers 1 and 4.

The cDNA of deletion variant Phl p 5a DM-Δ94-113, 175-198 (SEQ ID NO 7, cDNA sequence (723 bp), and SEQ ID NO 8, amino acid sequence (240 aa)) was likewise prepared from two cDNA fragments. The 5'-terminal fragment was generated using primers 1 and 5 and with rPhl p 5a wt-cDNA as matrix, and the 3'-terminal fragment was generated using primers 4 and 6 with Phl p 5a DM-Δ175-198-cDNA as matrix. By means of the common sequence region corresponding to amino acids 88-93 of the rPhl p 5a wt protein, the fragments were connected by a third PCR using primers 1 and 4, and the product was amplified.

The cDNAs encoding for the modified allergens were ligated into the expression vector pProExHT (Invitrogen, Carlsbad, USA) via the Ehel and HindIII restriction sites and subsequently sequenced in full.

The immunological cross reactivity of the group 5 allergens of the Pooideae, such as, for example, *Poe pratensis* and *Lolium perenne*, is based on a very similar amino acid sequence. It can be taken as certain that the corresponding genes go back to a common progenitor gene. Homologous sequence regions in the group 5 allergens of the Pooideae exist both for the sequences of deletions Δ94-113 and Δ175-198 of the Phl p 5a wt protein sequence (reference: GenBank AJ555152) and also for the flanking sequence regions thereof. The high homology of the sequence regions in question can be demonstrated both at the DNA level and also at the amino acid sequence level (FIG. 1 and FIG. 2).

TABLE 1

List of the PCR primers employed for the preparation of deletion variants

| Primer | SEQ ID NO | Direction | Sequence (5'→3') |
|---|---|---|---|
| 1 | 9 | sense | gcc gat cta ggc tac ggc ccg gcc |
| 2 | 10 | antisense | aac ata act agt ggc agc gac ctt gaa ggc ggc gtc |
| 3 | 11 | sense | atc ta act agt acg ggc ggc gcc tac gaga |
| 4 | 12 | antisense | aac ata aag ctt tca gac ttt gta gcc acc agt |
| 5 | 13 | antisense | gga gct gga ttc ggc ggc gcc ctt ggg |
| 6 | 14 | sense | gcc gcc gaa tcc agc tcc ggc gcg acg cct gag gcc aag tac gac |

The Spel Restriction Sites are Indicated by Underlining

Expression and Purification of Recombinant Phl p 5a Molecules

The recombinant proteins were expressed as histidine fusion proteins with integrated protease cleavage site (expression vector pProExHT; Invitrogen, Carlsbad, USA) for optional removal of the histidine fusion component (His) in *Escherichia coli* (strain JM109). rPhl p5a wt and the deletion mutants were firstly purified by specific binding of the N-terminal histidine residues to an Ni2+ chelate matrix (immobilised metal ion affinity chromatography, IMAC) and subsequently by preparative gel filtration (size exclusion chromatography, SEC).

The purity of the eluted proteins was monitored by SDS-PAGE and analytical SEC. The results showed that rPhl p 5a wt (His), Phl p 5a DM-Δ94-113 (His); Phl p 5a DM-Δ175-198 (His) and Phl p 5a DM-Δ94-113, 175-198 (His) could be prepared with high purity and in monomeric form (FIG. 3). The identity of the proteins was demonstrated by Phl p 5a-specific monoclonal antibodies.

The checking of the IgE reactivity by means of IgE binding techniques (immunoblotting, strip test, EAST inhibition test and basophil activation test) and the investigation of the T-cell reactivity was in addition carried out with test substances without a histidine fusion component.

Figure 4:
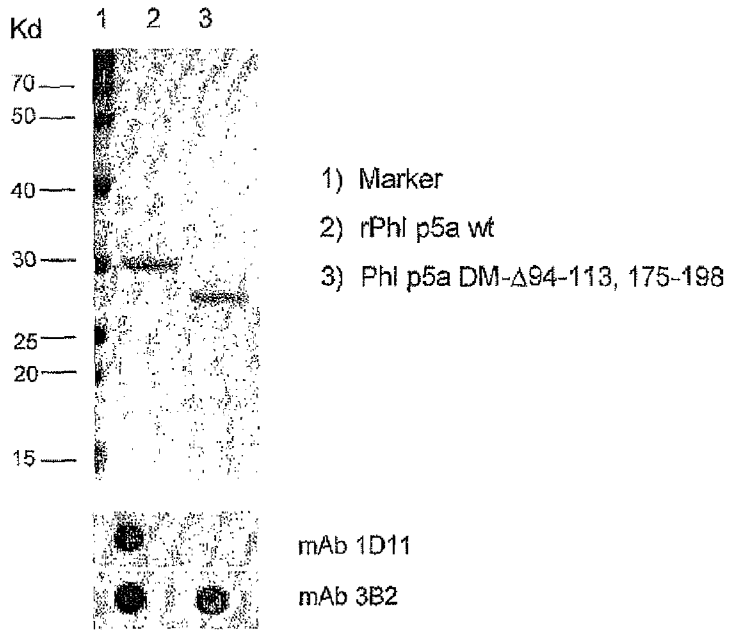
FIG. 4 shows SDS-PAGE of the purified non-fusion proteins Phl p 5a DM-D94-113, 175-198 and rPhl p 5a wt (top) and identity test with αPhl p 5 antibodies (bottom). Note: αPhl p 5 mAb Apha-1D11 binds region 175-198 (only rPhl p 5a wt is positive) and αPhl p 5a mAb Apha-3B2 binds a joint epitope of the two Phl p 5a molecules (both proteins positive). Abbreviation: mAb means monoclonal antibody.

To this end, the deletion variants was prepared in parallel to the comparative protein rPhl p 5a-wt firstly as fusion proteins. However, the histidine fusion component was subsequently cleaved off enzymatically (TEV protease, Invitrogen, Carlsbad, USA), leaving only a glycine as residue of the protease cleavage sequence on the N terminal of the target protein. Both the cleaved-off histidine component and also the protease used for the cleavage were separated off completely by IMAC. After preparative SEC, the purity and conformation of the eluted proteins was checked by SDS-PAGE and analytical SEC, as shown in FIGS. 4 and 5 for rPhl p 5a wt and the mutant Phl p 5a DM-Δ94-113, 175-198 respectively. All proteins were prepared in pure and monomeric form. An investigation by non-denaturing isoelectric focusing (IEF) of the non-fusion proteins always showed high homogeneity with respect to the surface charge (see FIG. 6, illustrative for Phl p 5a DM-Δ94-113, 175-198).

The identity of the recombinant proteins was demonstrated by the monoclonal anti-Phl p 5 antibodies (Allergopharma, Reinbek, Germany) Apha-1D11 or Apha-3B2 (see FIG. 4, illustrative for Phl p 5a DM-Δ94-113, 175-198) and N-terminal sequencing.

Determination of Reduced IgE Binding of the Phl p 5a Deletion Variants

A simple test method for determination of the IgE reactivity of allergenic molecules is investigation of the binding of specific IgE from the sera from allergy sufferers to membrane-bound test proteins by the strip test.

For this purpose, the test substances are bound in the same concentration and amount alongside one another to a strip of nitrocellulose membrane under non-denaturing conditions. A series of such membrane strips can be incubated in parallel with various sera from allergy sufferers. After a washing step, the specifically bound IgE antibodies are rendered visible on the membrane by a colour reaction promoted by an anti-hIgE/alkaline phosphatase conjugate.

The IgE reactivity of the recombinant proteins Phl p 5a wt (His), Phl p 5a DM-Δ94-113 (His), Phl p 5a DM-Δ175-198 (His) and Phl p 5a DM-Δ94-113, 175-198 (His) was investigated comparatively in the strip test using 43 individual sera from grass pollen allergy sufferers (FIG. 7).

All 43 sera from allergy sufferers contained Phl p 5a-specific IgE antibodies which reacted strongly with the natural Phl p 5a (nPhl p 5a, not shown here) and the recombinant equivalent rPhl p 5a wt (His).

Surprisingly, it became clear that the Phl p 5a-specific IgE antibodies of all 43 patient sera did not bind at all to deletion variant Phl p 5a DM-Δ94-113, 175-198 (His) or only did so to a very greatly reduced extent. The reduced IgE binding is attributable both to the deletion Δ94-113 and also to the deletion Δ175-198. Deletion variant Phl p 5a DM-Δ175-198 (His) shows a clearly recognisably reduced IgE binding capacity in this test in 35 of 43 sera from allergy sufferers. In some tests, the influence of the deletion of amino acids 175-198 was so great that IgE binding was virtually completely prevented (Ex.: P3, P20, P28)

The influence of deletion Δ94-113 on the IgE binding reactivity is less pronounced, but likewise clearly visible. Deletion variant Phl p 5a DM-Δ94-113 (His) was bound significantly more weakly by IgE of 19 of the 43 individual sera from allergy sufferers than the reference rPhl p 5a wt (His) (Ex.: P31, P37, P42). However, the reduction in the IgE binding was less drastically pronounced in many individual tests than the reduction caused by Δ175-198.

It is thus clear that both deletions contribute to the reduction in the total IgE binding reactivity of the deletion mutant Phl p 5a DM-Δ94-113, 175-198 (His).

In contrast to the strip test, the EAST Inhibition test (enzyme allergosorbent test) allows the investigation of allergen/IgE interactions in solution, enabling interfering masking of epitopes of the test substance by immobilisation on the membrane to be fundamentally excluded. The EAST inhibition test is carried out as follows. Microtitre plates are coated with allergens, here natural Phl p 5 (nPhl p 5a/b, mixture of Phl p 5a and Phl p 5b). After removal of the unbound allergen molecules by washing, the plate is blocked with bovine serum albumin in order to prevent later non-specific binding. IgE antibodies of allergy sufferers, as representative pool of individual sera (serum pool) or as single serum, is incubated in suitable dilution with the allergen-coated microtitre plates. The amount of allergen-bound IgE antibodies is quantified photometrically via an enzyme coupled to a second antibody (anti-hIgE/alkaline phosphatase conjugate) through conversion of a substrate into a coloured end product.

The binding of the IgE antibodies is inhibited substance-specifically by a soluble allergen or the substance to be tested (recombinant modified allergen) depending on the concentration. Immunochemically identical substances show identical inhibition curves.

The reference molecules used in this work were nPhl p 5, rPhl p 5a wt, and the histidine fusion protein rPhl p 5a wt (His). Besides other molecules, the IgE binding of the histidine fusion proteins Phl p 5a DM-Δ94-113 (His), Phl p 5a DM-Δ175-198 (His) and Phl p 5a DM-Δ94-113, 175-198 (His) and that of the non-fusion protein Phl p 5a DM-Δ94-113, 175-198 was investigated by comparison with these references.

FIGS. 8 *a-c* show representatively the specific inhibition curves of test substances raised with two individual sera and a serum pool of grass pollen allergy sufferers. nPhl p 5a/b showed the greatest inhibitory effect in all tests (about 80-95% inhibitory effect at a concentration of 10 μg/ml). The inhibitory effect of rPhl p 5a was significantly lower with a maximum inhibition of 70-80%. This effect is caused by the composition of nPhl p 5a/b, which also contains the isoform Phl p 5b in addition to the isoform Phl p 5a. The specific IgE antibodies against Phl p 5b cannot be inhibited by rPhl p 5a wt.

The histidine fusion component showed no effect on IgE binding. This is clear in all tests through the identical inhibition curves of rPhl p 5a wt (His) and rPhl p 5a wt. This demonstrates the validity of tests with histidine fusion proteins.

In general, two groups of patient sera were distinguished with respect to qualitative IgE binding.

The first group is represented by individual serum P15 (FIG. 8 *a*). These sera from allergy sufferers contained IgE antibodies whose binding to Phl p 5a was reduced by both deletions, Δ94-113 and Δ175-198. Deletion mutant Phl p 5a DM-Δ94-113 (His) showed only a maximum inhibitory effect of about 50% here, and the deletion mutant Phl p 5a DM-175-198 (His) showed an inhibitory effect of only 20-30%.

The double deletion mutant Phl p 5a DM-Δ94-113, 175-198 (His) was only able to inhibit the binding of IgE antibodies by 0-10% at the highest concentration employed. The use of the non-fusion protein Phl p 5a DM-Δ94-113, 175-198 confirmed this result (0-10% maximum IgE inhibition).

The second group of sera from allergy sufferers, represented by individual serum P44 (FIG. 8 *b*), differed from the first group through the fact that the IgE antibodies present in the sera reacted equally well with Phl p 5a DM-Δ94-113

(His) as with the reference rPhl p 5a wt (His) (70-80% maximum inhibition), whereas no or non-detectable amounts of IgE antibodies reacted with Phl p 5a DM-Δ175-198 (His) (0-10% maximum inhibition).

The double deletion mutant Phl p 5a DM-Δ94-113, 175-198 likewise showed a greatly reduced inhibitory effect (0-10%) with this group of sera from allergy sufferers, which was shown both for the fusion protein and also for the fusion component-free protein.

The sera of these allergy sufferers apparently contained IgE antibodies directed principally against epitopes of the C-terminal part of the molecule.

The measurement data of the IgE binding reactivity of IgE antibodies of a serum pool of 20 allergy sufferers underline the importance of the deletions Δ94-113 and Δ175-198 for the reduction in the IgE binding of Phl p 5a (FIG. 8 *c*). Both individual deletion mutants, Phl p 5a DM-Δ94-113 (His) and Phl p 5a DM-Δ175-198 (His) show a lower maximum inhibitory effect, of 40-50% and about 30% respectively, than rPhl p 5a wt (about 70%). The double deletion mutant Phl p 5a DM-Δ94-113, 175-198 was only bound very weakly by the IgE antibodies of the serum pool (10-15% maximum inhibition), which, in agreement with the test of 43 allergy sufferers in the strip test, indicates greatly reduced IgE binding reactivity of this Phl p 5a variant in very many, if not all, grass pollen allergy sufferers.

Determination of the Hypoallergeneity of the Deletion Mutants by Basophil Activation Test By means of a basophil activation test, the effects of reduced IgE binding ability of the deletion mutants on the functional effect in the crosslinking of membrane-bound IgE of the effector cells and activation thereof were investigated. The functional reduction in allergeneity was thus measured in a sensitive in-vitro test.

For the basophil activation test, heparinised full blood from grass pollen allergy sufferers is incubated with various concentrations of the test substances. Allergenic substances are able to bind specific IgE antibodies, which are associated with the high-affinity IgE receptors of the basophilic granulocytes.

Crosslinking of the IgE/receptor complexes initiated by the allergen molecules results in signal transduction, which results in degranulation of the effector cells and thus initiation of the allergic reactions in vivo.

In vitro, allergen-induced activation of basophilic immunocytes can be determined by quantification of the expression of a surface protein (CD203c) coupled to signal transduction of the IgE receptor crosslinking (Kahlert et al., Clinical Immunology and Allergy in Medicine Proceedings of the EAACI-2002 (2003) Naples, Italy 739-744). The number of expressed surface proteins on a cell and the percentage of activated cells of a cell pool is measured highly sensitively via the binding of a fluorescencelabelled monoclonal antibody to the surface protein and subsequent analysis by fluorescence-activated flow cytometry.

The reference substances employed here were both purified natural Phl p 5a (nPhl p 5a) and also rPhl p5a wt in parallel with the test substances. The test results of the double deletion mutant Phl p 5a DM Δ94-113, 175-198 with basophils from six test persons are shown as curves in FIG. 9. The test results with basophils from a total of 10 clinically defined allergy sufferers are shown in Table 2.

The A50 values (A50: allergen concentration at 50% of the number of basophils activated to the maximum) of the reference molecules were, varying individually, between ~1.3-15 pM for rPhl p 5a wt and ~0.3-10 pM for nPhl p 5a (Table 2). By contrast, the A50 values of deletion variant Phl p 5a DM Δ94-113, 175-198 were between ~18-8400 pM.

The A50 values determined for the three substances employed were used to determine the allergenic efficacy of deletion variant Phl p 5a DM Δ94-113, 175-198 in relation to the unchanged reference molecules nPhl p 5a and rPhl p5a wt for each test person (Table 2).

The relative allergenic efficacy (Pr, relative potency) of deletion variant Phl p 5a DM Δ94-113, 175-198 was reduced between ~12-5000 fold compared with the reference rPhl p 5a wt or ~16-32000 fold compared with the reference nPhl p 5a (Table 2).

TABLE 2

Determination of the hypoallergeneity of deletion mutant Phl p 5a DM-Δ94-113, 175-198 by means of basophil activation test

| Donor[c] | Test substance $A_{50}$ [pM][a] nPhl p 5a | rPhl p 5a wt | Phl p 5a DM-Δ94-113, 175-198 | Pr value[b] Phl p 5a DM-Δ94-113, 175-198 relative to rPhl p 5a wt[d] | Pr value[b] Phl p 5a DM-Δ94-113, 175-198 relative to nPhl p 5a[e] |
|---|---|---|---|---|---|
| P13 | 4.08 | 5.34 | 477.2 | 0.0111 | 0.0085 |
| P17 | 6.44 | 2.68 | 466.6 | 0.0057 | 0.0137 |
| P20 | 0.26 | 1.68 | 8433.0 | **0.0002**[f] | **0.00003**[f] |
| P23 | 1.02 | 1.26 | 39.2 | 0.0321 | 0.0260 |
| P24 | 1.22 | 2.57 | 58.1 | 0.0442 | 0.0209 |
| P28 | 9.43 | 11.35 | 198.2 | 0.0573 | 0.0476 |
| P29 | 1.77 | 2.34 | 33.7 | 0.0694 | 0.0525 |
| P31 | 10.15 | 14.66 | 3967.0 | 0.0037 | 0.0026 |
| P34 | 3.48 | 2.54 | 165.1 | 0.0153 | 0.0211 |
| P40 | 1.08 | 1.45 | 17.5 | **0.0829** | **0.0617** |

[a]Allergen concentration at 50% of the number of basophils activated to the maximum
[b]Relative potency
[c]Clinically defined grass pollen allergy sufferers
[d]Calculated from A50 rPhl p 5a wt/A50 Phl p 5a DM-Δ94-113, 175-198
[e]Calculated from A50 nPhl p.5a/A50 Phl p 5a DM-Δ94-113, 175-198
[f]Bold: minimum and maximum values T-Cell Reactivity T helper lymphocytes react with peptide fragments of the allergens (approx. 12-25 amino acids) formed by enzymatic degradation in antigen-presenting cells (APCs) and are presented to the T-cells after inclusion of the suitable peptides in the individual MHC class II molecules at the surface of the APCs. This allergen-specific activation of the T helper lymphocytes is the prerequisite for subsequent reactions (proliferation, anergy, apoptosis) and for functional differentiation (TH1 and TH2). The influencing of allergen-specific T-lymphocytes by treatment with an allergen or an allergen variant in hyposensitisation is regarded as the key for the therapeutic efficacy. In order to investigate T-cell reactivity, oligoclonal T-cell lines (TCLs) of Graminae pollen allergy sufferers are established by conventional methods with stimulation by nPhl p5 or rPhl p 5 molecules.

In a proliferation test, the various T-cell lines were stimulated with the reference allergens nPhl p5a and rPhl p5a wt and the double deletion mutant Phl p 5a DM Δ94-113, 175-198. The proliferation rate was determined by the incorporation of [$^3$H]thymidine by conventional methods.

TABLE 3

Determination of the T-cell reactivity of deletion mutant Phl p 5a DM-Δ94-113, 175-198 by means of proliferation tests with Phl p 5-specific T-cell lines (TCLs)

| | | Stimulation index[a] | | |
|---|---|---|---|---|
| Donor[b] | TCL | nPhl p 5a | rPhl p 5a wt | Phl p 5a DM-Δ94-113, 175-198 |
| A | 3.2 | 9.8 | 4.9 | 4.4 |
| B | 8.2 | 21.0 | 15.5 | 13.3 |
| C | 11.2 | 5.2 | 4.7 | 7.2 |
| C | 11.3 | 3.3 | 2.9 | 3.5 |
| C | 11.43 | 3.0 | 3.9 | 2.6 |
| D | 19.1 | 6.5 | 4.7 | 7.5 |
| D | 19.2 | 9.6 | 3.3 | 2.6 |
| E | 23.22 | 21.8 | 29.0 | 20.8 |
| E | 23.50 | 7.5 | 8.4 | 6.6 |
| F | 89.23 | 1.8 | 3.5 | 1.8 |

[a]Calculated from [$^3$H] measurement values. cpm measurement values of allergen-stimulated cell cultures/cpm measurement values of unstimulated cell cultures
[b]Donor: clinically defined grass pollen allergy sufferers The results with ten TCLs from six allergy sufferers show that these TCLs were stimulated to proliferation by Phl p 5a DM Δ94-113, 175-198 in comparable strength as by the unchanged natural or recombinant wild-type allergen (Table 3).

The present invention thus relates to variants of the group 5 allergens of the Pooideae which are characterised by reduced IgE reactivity compared with the known wild-type allergens and by retained reactivity with T-lymphocytes. These group 5 allergens are preferably Phl p 5a, Poa p 5 and Lol p 5, very particularly preferably Phl p 5a.

As it has proven particularly favourable for the purposes of the invention for amino-acid sequence regions which correspond to amino-acid sequence regions 94-113 and 175-198 of Phl p 5a to be missing or removed in the group 5 allergens, this invention relates, in particular, to such allergen variants. The first-mentioned or second-mentioned region may be missing individually, but also both said regions may be missing simultaneously, with the latter embodiment being very particularly preferred.

Owing to the high sequence homologies within the group 5 allergens from Pooideae, these regions can be unambiguously identified in sequence alignments of the Phl p 5a sequence with sequences from other group 5 allergens. The above-described allergen variants preferably originate from Phl p 5a or correspond to the sequences in accordance with SEQ ID NO 4, 6 or 8.

The allergen variants according to the invention can be prepared starting from the cloned DNA sequence with the aid of genetic engineering methods. In principle, however, chemical modifications of the native allergen extract are also possible (Fiebig, 1995, Allergo J. 4 (7), 377-382).

Naturally, further modifications in other positions—for example in order to increase the hypoallergeneity—are also possible via the variations of group 5 allergens described in the present patent application. These modifications can be, for example, amino acid insertions, deletions and exchanges, cleavage of the protein into fragments and fusion of the protein or fragments thereof with other proteins or peptides.

During preparation of the allergen variants described in more detail here, an His tag was introduced by genetic engineering methods for the purposes of improved purification of the overexpressed proteins.

The invention furthermore relates to a DNA molecule encoding for an allergen variant described above, in particular corresponding to a sequence in accordance with SEQ ID NO 3, 5 or 7, to a recombinant expression vector containing this DNA molecule, and to a host organism transformed with said DNA molecule or said expression vector. Suitable host organisms may be prokaryotic or eukaryotic, single- or multicelled organisms, such as bacteria or yeasts. A host organism which is preferred in accordance with the invention is *E. coli.*

The invention furthermore relates to a process for the preparation of an allergen variant according to the invention by cultivation of the said host organism and isolation of the corresponding allergen variant from the culture.

The present invention additionally relates to the allergen variants, DNA molecules and expression vectors described above in their property as medicaments.

The present invention furthermore relates to pharmaceutical compositions comprising at least one of these allergen variants or a corresponding DNA molecule or a corresponding expression vector and optionally further active ingredients and/or adjuvants for the treatment of allergies in the triggering of which group 5 allergens of the Pooideae are involved, or for the immunotherapeutic vaccination of patients having allergies in the triggering of which group 5 allergens of the Pooideae are involved and/or for the prevention of such allergies.

If these are pharmaceutical compositions of the second type (comprising at least one DNA molecule or an expression vector), these compositions preferably furthermore comprise aluminium hydroxide, an immunostimulatory CpG-containing oligonucleotide or a combination of the two as adjuvants.

For the purposes of this invention, pharmaceutical compositions can be used as therapeutic agents in human or veterinary medicine. Suitable excipients are organic or inorganic substances which are suitable for parenteral administration and do not react with group 5 allergen variants according to the invention. Suitable for parenteral administration are, in particular, solutions, preferably oily or aqueous solutions, furthermore suspensions, emulsions or implants. The allergen variants according to the invention may also be lyophilised and the resultant lyophilisates used, for example, for the preparation of injection preparations. The compositions indicated may be sterilised and/or comprise adjuvants, such as lubricants, preservatives, stabilisers and/or wetting agents, emulsifiers, salts for modifying the osmotic pressure, buffer substances and/or a plurality of further active ingredients.

Furthermore, appropriate formulation of the allergen variants according to the Invention enables depot preparations to be obtained, for example by adsorption on aluminium hydroxide.

Finally, the present invention relates to the use of at least one allergen variant according to the invention or a DNA molecule according to the invention or an expression vector according to the invention for the preparation of a medicament for the treatment of allergies in the triggering of which group 5 allergens of the Pooideae are involved or for the immunotherapeutic vaccination of patients having allergies in the triggering of which group 5 allergens of the Pooideae are involved and/or for the prevention of such allergies.

The invention claimed is:

1. A DNA molecule comprising a DNA sequence selected from the group consisting of SEQ ID NO: 3, SEQ ID NO: 5 or SEQ ID NO: 7.

2. A recombinant expression vector containing a DNA molecule according to claim 1, functionally bonded to an expression control sequence.

3. A host organism transformed with a DNA molecule according to claim 1 or an expression vector containing the DNA molecule and an expression control sequence.

4. A medicament comprising a DNA molecule of claim 1 and a carrier.

5. A medicament comprising a recombinant expression vector of claim 2 and a carrier.

6. A pharmaceutical composition comprising
- at least one DNA molecule of claim 1 or at least one expression vector containing said DNA molecule and an expression control sequence; and
- a pharmaceutically acceptable carrier;
- optionally together with an active ingredient or adjuvant.

7. The pharmaceutical composition of claim 6, wherein the adjuvant is aluminium hydroxide, an immunostimulatory CpG-containing oligonucleotide or a combination thereof.

8. A method to reduce the likelihood or symptoms of an allergic reaction triggered by group 5 allergens of Pooideae in a subject in need thereof, comprising administering to said subject in a DNA molecule of claim 1 or an expression vector comprising said DNA molecule and an expression control sequence.

9. A nucleic acid molecule which encodes a polypeptide selected from the group consisting of:
- (a) a polypeptide consisting of amino acids 1-37 and 58-206 of SEQ ID NO: 19;
- (b) a polypeptide consisting of amino acids 1-118 and 143-206 of SEQ ID NO: 19;
- (c) a polypeptide consisting of amino acids 1-37, 58-118 and 143-206 of SEQ ID NO: 19;
- (d) a polypeptide consisting of amino acids 1-33 and 54-204 of SEQ ID NO: 20;
- (e) a polypeptide consisting of amino acids 1-116 and 141-204 of SEQ ID NO: 20;
- (f) a polypeptide consisting of amino acids 1-33, 54-116 and 141-204 of SEQ ID NO: 20;
- (g) a polypeptide consisting of amino acids 1-39 and 60-208 of SEQ ID NO: 21;
- (h) a polypeptide consisting of amino acids 1-120 and 145-208 of SEQ ID NO: 21;
- (i) a polypeptide consisting of amino acids 1-39, 60-120 and 145-208 of SEQ ID NO: 21;
- (j) a polypeptide consisting of amino acids 1-39 and 60-210 of SEQ ID NO: 22;
- (k) a polypeptide consisting of amino acids 1-122 and 147-210 of SEQ ID NO: 22; and
- (l) a polypeptide consisting of amino acids 1-39, 60-210 and 147-210 of SEQ ID NO: 22.

10. The nucleic acid molecule of claim 9, which is a DNA molecule.

11. A recombinant expression vector containing a DNA molecule according to claim 10, functionally bonded to an expression control sequence.

12. A host organism transformed with a DNA molecule according to claim 10 or an expression vector containing the DNA molecule and an expression control sequence.

13. A process for the preparation of an allergen variant of group 5 allergens of Pooideae, comprising cultivating a host organism transformed with a DNA of claim 10 or a vector containing the DNA molecule and an expression control sequence under conditions sufficient for the expression of the allergen variant; and isolating the allergen variant from the culture.

14. A medicament comprising a DNA molecule of claim 10 and a carrier.

15. A medicament comprising a recombinant expression vector of claim 11 and a carrier.

16. A pharmaceutical composition comprising at least one DNA molecule of claim 10 or at least one expression vector containing said DNA molecule and an expression control sequence; and a pharmaceutically acceptable carrier;

optionally together with an active ingredient or adjuvant.

17. The pharmaceutical composition of claim 16, wherein the adjuvant is aluminium hydroxide, an immunostimulatory CpG-containing oligonucleotide or a combination thereof.

18. A method to reduce the likelihood or symptoms of an allergic reaction triggered by group 5 allergens of Pooideae in a subject in need thereof, comprising administering to said subject a DNA molecule of claim 10 or an expression vector comprising said DNA molecule and an expression control sequence.

19. The pharmaceutical composition of claim 6, which is effective to reduce the likelihood or symptoms of an allergic reaction that are triggered by group 5 allergens of Pooideae.

20. The pharmaceutical composition of claim 16, which is effective to reduce the likelihood or symptoms of an allergic reaction that are triggered by group 5 allergens of Pooideae.

* * * * *